(12) United States Patent
Swift et al.

(10) Patent No.: US 12,377,010 B2
(45) Date of Patent: Aug. 5, 2025

(54) EXOSKELETON DATA LABELING SYSTEM AND METHOD

(71) Applicant: Roam Robotics Inc., San Francisco, CA (US)

(72) Inventors: Timothy Alan Swift, Albany, CA (US); Nicolas Cox, Mountain View, CA (US); Kevin Conrad Kemper, San Francisco, CA (US)

(73) Assignee: ROAM ROBOTICS INC., San Francisco, CA (US)

( * ) Notice: Subject to any disclaimer, the term of this patent is extended or adjusted under 35 U.S.C. 154(b) by 711 days.

(21) Appl. No.: 16/862,400

(22) Filed: Apr. 29, 2020

(65) Prior Publication Data

US 2020/0253808 A1    Aug. 13, 2020

Related U.S. Application Data

(63) Continuation of application No. 15/887,866, filed on Feb. 2, 2018, now Pat. No. 11,259,979.
(Continued)

(51) Int. Cl.
*A61H 3/00* (2006.01)
*A61H 1/02* (2006.01)
(Continued)

(52) U.S. Cl.
CPC ............. *A61H 3/00* (2013.01); *A61H 1/0237* (2013.01); *A61H 1/0274* (2013.01);
(Continued)

(58) Field of Classification Search
CPC ...... A61H 3/00; A61H 1/0237; A61H 1/0274; A61H 2003/001; A61H 2201/1238;
(Continued)

(56) References Cited

U.S. PATENT DOCUMENTS

| | | | |
|---|---|---|---|
| 440,684 | A | 11/1890 | Yagn |
| 3,823,711 | A | 7/1974 | Hatton |

(Continued)

FOREIGN PATENT DOCUMENTS

| | | |
|---|---|---|
| CN | 101151071 A | 3/2008 |
| CN | 101960441 A | 1/2011 |

(Continued)

OTHER PUBLICATIONS

Chinese Patent Office Second Office Action and Supplementary Search Report dated Apr. 25, 2022; Application No. 201880023218.5; 15 pages.

(Continued)

*Primary Examiner* — Justine R Yu
*Assistant Examiner* — Christopher E Miller
(74) *Attorney, Agent, or Firm* — Davis Wright Tremaine LLP

(57) ABSTRACT

An exoskeleton network. The exoskeleton network includes an exoskeleton system that has one or more sensors and a memory; a user device that is local to the exoskeleton system and that operably communicates with the exoskeleton system; and a classification server that operably communicates with at least one of the exoskeleton system and the user device. The exoskeleton network performs feature extraction on sensor data obtained from the one or more sensors to generate feature-extracted sensor data and performs label derivation on the feature-extracted sensor data to generate labeled sensor data.

20 Claims, 12 Drawing Sheets

Related U.S. Application Data

(60) Provisional application No. 62/454,575, filed on Feb. 3, 2017.

(51) Int. Cl.
*G05B 13/02* (2006.01)
*G06F 8/65* (2018.01)
*G16H 20/30* (2018.01)
*G16H 40/63* (2018.01)
*G16H 40/67* (2018.01)
*G16H 50/20* (2018.01)
*G16H 50/30* (2018.01)
*G16H 50/50* (2018.01)
*G16H 50/70* (2018.01)

(52) U.S. Cl.
CPC ....... *G05B 13/026* (2013.01); *G05B 13/0265* (2013.01); *G06F 8/65* (2013.01); *G16H 20/30* (2018.01); *G16H 40/63* (2018.01); *G16H 40/67* (2018.01); *G16H 50/20* (2018.01); *G16H 50/30* (2018.01); *G16H 50/50* (2018.01); *G16H 50/70* (2018.01); *A61H 2003/001* (2013.01); *A61H 2201/1238* (2013.01); *A61H 2201/164* (2013.01); *A61H 2201/165* (2013.01); *A61H 2201/5007* (2013.01); *A61H 2201/501* (2013.01); *A61H 2201/5023* (2013.01); *A61H 2201/5038* (2013.01); *A61H 2201/5043* (2013.01); *A61H 2201/5046* (2013.01); *A61H 2201/5058* (2013.01); *A61H 2201/5061* (2013.01); *A61H 2201/5064* (2013.01); *A61H 2201/5084* (2013.01); *A61H 2205/10* (2013.01)

(58) Field of Classification Search
CPC ........ A61H 2201/164; A61H 2201/165; A61H 2201/5007; A61H 2201/501; A61H 2201/5023; A61H 2201/5038; A61H 2201/5043; A61H 2201/5046; A61H 2201/5058; A61H 2201/5061; A61H 2201/5064; A61H 2201/5084; A61H 2205/10; A61H 2003/005; G05B 13/026; G05B 13/0265; G06F 8/65; G16H 20/30; G16H 40/63; G16H 40/67; G16H 50/20; G16H 50/30; G16H 50/50; G16H 50/70; B25J 9/142; A61F 2/68
See application file for complete search history.

(56) References Cited

U.S. PATENT DOCUMENTS

| | | | |
|---|---|---|---|
| 3,868,952 A | 3/1975 | Hatton | |
| 3,982,531 A | 9/1976 | Shaffer | |
| 3,993,056 A | 11/1976 | Rabischong et al. | |
| 4,274,399 A | 6/1981 | Mummert | |
| 4,408,600 A | 10/1983 | Davis | |
| 4,523,582 A | 6/1985 | Barber | |
| 4,623,158 A | 11/1986 | Monreal | |
| 4,671,258 A | 6/1987 | Barthlome | |
| 4,944,755 A | 7/1990 | Hennequin et al. | |
| 4,953,856 A | 9/1990 | Fox, III | |
| 5,033,457 A | 7/1991 | Bonutti | |
| 5,067,302 A | 11/1991 | Boeckmann | |
| 5,169,169 A | 12/1992 | Crawford | |
| 5,295,704 A | 3/1994 | Flock | |
| 5,483,838 A | 1/1996 | Holden | |
| 5,780,123 A | 7/1998 | Kamiyama et al. | |
| 5,951,048 A | 9/1999 | Slaughter | |
| 6,117,507 A | 9/2000 | Smith | |
| 6,248,463 B1 | 6/2001 | Dopp et al. | |
| 6,612,340 B1 | 9/2003 | Lause | |
| 6,776,769 B2 | 8/2004 | Smith | |
| 7,086,322 B2 | 8/2006 | Schulz | |
| 7,479,121 B2 | 1/2009 | Branch | |
| 7,628,766 B1 | 12/2009 | Kazerooni et al. | |
| 8,171,570 B2 | 5/2012 | Adarraga | |
| 8,784,350 B2 | 7/2014 | Cohen | |
| 9,205,560 B1 | 12/2015 | Edsinger et al. | |
| 9,709,206 B2 | 7/2017 | Duttenhoefer et al. | |
| 9,821,475 B1 | 11/2017 | Lynn et al. | |
| 9,827,667 B2 | 11/2017 | Griffith et al. | |
| 9,995,321 B2 | 6/2018 | Lynn et al. | |
| 10,012,229 B2 | 7/2018 | Lynn et al. | |
| 10,245,204 B2 | 4/2019 | Sandler et al. | |
| 10,543,110 B2 | 1/2020 | Piercy et al. | |
| 10,548,800 B1 | 2/2020 | Barnes | |
| 10,562,180 B2 | 2/2020 | Telleria et al. | |
| 10,605,365 B1 | 3/2020 | Griffith et al. | |
| 10,611,020 B2 | 4/2020 | Griffith et al. | |
| 10,619,633 B2 | 4/2020 | Lynn et al. | |
| 10,702,742 B2 | 7/2020 | Sharma et al. | |
| 10,780,011 B2 | 9/2020 | Yang et al. | |
| 10,780,012 B2 | 9/2020 | Lamb et al. | |
| 10,966,895 B2 | 4/2021 | Lamb et al. | |
| 11,033,450 B2 | 6/2021 | Lamb et al. | |
| 11,191,653 B2 | 12/2021 | Grandmaison et al. | |
| 11,213,417 B2 | 1/2022 | Piercy et al. | |
| 11,254,002 B1 | 2/2022 | Ebrahimi Afrouzi et al. | |
| 11,259,979 B2 | 3/2022 | Swift et al. | |
| 11,351,083 B2 | 6/2022 | Swift et al. | |
| 11,498,203 B2 | 11/2022 | Ding et al. | |
| 11,780,186 B1 | 10/2023 | Swierkocki et al. | |
| 11,801,153 B2 * | 10/2023 | Bulea | A61F 2/70 |
| 2001/0029343 A1 | 10/2001 | Seto et al. | |
| 2002/0026794 A1 | 3/2002 | Shahinpoor et al. | |
| 2004/0010720 A1 | 1/2004 | Singh et al. | |
| 2004/0140295 A1 | 7/2004 | Herres | |
| 2004/0176715 A1 | 9/2004 | Nelson | |
| 2005/0066810 A1 | 3/2005 | Schulz | |
| 2005/0102863 A1 | 5/2005 | Hannon et al. | |
| 2005/0107726 A1 * | 5/2005 | Oyen | G16H 40/67 602/16 |
| 2005/0124924 A1 | 6/2005 | Slautterback et al. | |
| 2005/0177082 A1 | 8/2005 | Bledsoe | |
| 2006/0069336 A1 | 3/2006 | Krebs et al. | |
| 2006/0128538 A1 | 6/2006 | Sato et al. | |
| 2006/0161220 A1 | 7/2006 | Kobayashi et al. | |
| 2006/0173552 A1 | 8/2006 | Roy | |
| 2006/0184280 A1 * | 8/2006 | Oddsson | A61F 2/60 623/24 |
| 2006/0207726 A1 | 9/2006 | Driver et al. | |
| 2006/0211956 A1 * | 9/2006 | Sankai | A61F 5/0102 601/5 |
| 2007/0042710 A1 | 2/2007 | Mahini et al. | |
| 2007/0061107 A1 | 3/2007 | Vock et al. | |
| 2007/0075543 A1 | 4/2007 | Marx et al. | |
| 2007/0239087 A1 | 10/2007 | Kivisto | |
| 2008/0009771 A1 | 1/2008 | Perry et al. | |
| 2008/0161937 A1 | 7/2008 | Sankai | |
| 2008/0195005 A1 | 8/2008 | Horst et al. | |
| 2008/0234608 A1 | 9/2008 | Sankai | |
| 2008/0287850 A1 | 11/2008 | Adarraga | |
| 2009/0024061 A1 | 1/2009 | Ueda et al. | |
| 2009/0118656 A1 | 5/2009 | Ingimundarson et al. | |
| 2009/0179112 A1 | 7/2009 | Gu | |
| 2009/0198164 A1 | 8/2009 | Krause | |
| 2009/0276058 A1 | 11/2009 | Ueda et al. | |
| 2010/0040936 A1 | 2/2010 | Pozin et al. | |
| 2010/0094188 A1 | 4/2010 | Goffer et al. | |
| 2010/0106065 A1 | 4/2010 | Ward | |
| 2010/0114329 A1 | 5/2010 | Casler et al. | |
| 2010/0204627 A1 | 8/2010 | Kazerooni et al. | |
| 2010/0217169 A1 | 8/2010 | Ingimundarson | |
| 2010/0249675 A1 | 9/2010 | Fujimoto et al. | |
| 2010/0270771 A1 | 10/2010 | Kobayashi et al. | |
| 2010/0280424 A1 | 11/2010 | Kawakami et al. | |
| 2010/0292556 A1 * | 11/2010 | Golden | G16H 40/40 607/31 |
| 2011/0059355 A1 | 3/2011 | Zhang et al. | |
| 2011/0066088 A1 | 3/2011 | Little et al. | |

(56) References Cited

U.S. PATENT DOCUMENTS

| | | | |
|---|---|---|---|
| 2011/0071417 A1 | 3/2011 | Liu et al. | |
| 2011/0099026 A1 | 4/2011 | Oakley et al. | |
| 2011/0105966 A1 | 5/2011 | Kazerooni et al. | |
| 2011/0105969 A1 | 5/2011 | Nace | |
| 2011/0112447 A1 | 5/2011 | Hsiao-Wecksler et al. | |
| 2011/0118635 A1 | 5/2011 | Yamamoto | |
| 2011/0186208 A1 | 8/2011 | Cartabbia et al. | |
| 2011/0290798 A1 | 12/2011 | Corbett et al. | |
| 2012/0059291 A1 | 3/2012 | Nguyen | |
| 2012/0259429 A1* | 10/2012 | Han | A61F 5/0127 623/24 |
| 2012/0259431 A1* | 10/2012 | Han | A61H 1/024 623/24 |
| 2012/0271211 A1 | 10/2012 | Bledsoe | |
| 2012/0289870 A1 | 11/2012 | Hsiao-Wecksler et al. | |
| 2012/0316477 A1 | 12/2012 | Hamaya et al. | |
| 2012/0328824 A1 | 12/2012 | Cartabbia et al. | |
| 2013/0053736 A1 | 2/2013 | Konishi | |
| 2013/0150980 A1 | 6/2013 | Swift et al. | |
| 2013/0158445 A1 | 6/2013 | Kazerooni et al. | |
| 2013/0172797 A1 | 7/2013 | Merkley et al. | |
| 2013/0197408 A1 | 8/2013 | Goldfarb et al. | |
| 2013/0245512 A1 | 9/2013 | Goffer et al. | |
| 2013/0289452 A1 | 10/2013 | Smith et al. | |
| 2013/0296758 A1 | 11/2013 | Castillo | |
| 2013/0333368 A1 | 12/2013 | Durfee et al. | |
| 2014/0109560 A1 | 4/2014 | Ilievski et al. | |
| 2014/0124557 A1 | 5/2014 | Velarde | |
| 2014/0148745 A1 | 5/2014 | Castillo | |
| 2014/0148747 A1 | 5/2014 | Fleming | |
| 2014/0171838 A1* | 6/2014 | Aleksov | A61H 3/00 601/33 |
| 2014/0207037 A1 | 7/2014 | Horst | |
| 2014/0212243 A1 | 7/2014 | Yagi et al. | |
| 2014/0276264 A1 | 9/2014 | Caires et al. | |
| 2014/0277739 A1 | 9/2014 | Kornbluh et al. | |
| 2014/0318118 A1 | 10/2014 | Mazzeo et al. | |
| 2014/0358290 A1 | 12/2014 | Kazerooni et al. | |
| 2015/0005685 A1 | 1/2015 | Chetlapalli et al. | |
| 2015/0068636 A1 | 3/2015 | Duttenhoefer et al. | |
| 2015/0088043 A1 | 3/2015 | Goldfield et al. | |
| 2015/0108191 A1 | 4/2015 | Velarde | |
| 2015/0126911 A1 | 5/2015 | Abramowicz et al. | |
| 2015/0134080 A1 | 5/2015 | Roh | |
| 2015/0157525 A1* | 6/2015 | Choi | A61H 1/024 700/245 |
| 2015/0173927 A1 | 6/2015 | Castillo | |
| 2015/0173993 A1 | 6/2015 | Walsh et al. | |
| 2015/0209214 A1 | 7/2015 | Herr et al. | |
| 2015/0285238 A1 | 10/2015 | Lynn et al. | |
| 2015/0290794 A1 | 10/2015 | Griffith et al. | |
| 2015/0302162 A1* | 10/2015 | Hughes | G16H 40/67 702/19 |
| 2015/0351991 A1 | 12/2015 | Amundson et al. | |
| 2015/0351995 A1 | 12/2015 | Zoss et al. | |
| 2015/0366696 A1 | 12/2015 | Ingimundarson et al. | |
| 2016/0008157 A1 | 1/2016 | Brookover et al. | |
| 2016/0045386 A1 | 2/2016 | Sandler et al. | |
| 2016/0051389 A1 | 2/2016 | Seligman | |
| 2016/0058647 A1 | 3/2016 | Maddry | |
| 2016/0074272 A1* | 3/2016 | Ahn | A61B 5/4851 623/24 |
| 2016/0082319 A1 | 3/2016 | Macri et al. | |
| 2016/0089591 A1 | 3/2016 | Williamson | |
| 2016/0107309 A1 | 4/2016 | Walsh et al. | |
| 2016/0120683 A1 | 5/2016 | Romo et al. | |
| 2016/0143800 A1* | 5/2016 | Hyung | A61H 3/00 623/32 |
| 2016/0158087 A1 | 6/2016 | Huang et al. | |
| 2016/0184166 A1 | 6/2016 | Takenaka et al. | |
| 2016/0213548 A1 | 7/2016 | John et al. | |
| 2016/0235616 A1 | 8/2016 | Goffer et al. | |
| 2016/0242986 A1 | 8/2016 | Nagata et al. | |
| 2016/0242987 A1 | 8/2016 | Nagata et al. | |
| 2016/0252110 A1 | 9/2016 | Galloway et al. | |
| 2016/0261224 A1 | 9/2016 | Madrone et al. | |
| 2016/0278948 A1 | 9/2016 | Piercy et al. | |
| 2016/0297504 A1 | 10/2016 | Saindon et al. | |
| 2016/0300156 A1 | 10/2016 | Bowers et al. | |
| 2016/0302955 A1 | 10/2016 | Siddiqui et al. | |
| 2016/0331557 A1 | 11/2016 | Tong et al. | |
| 2016/0331560 A1 | 11/2016 | Tong et al. | |
| 2016/0331624 A1 | 11/2016 | Sankai et al. | |
| 2016/0346156 A1 | 12/2016 | Walsh et al. | |
| 2017/0018761 A1 | 1/2017 | Ogino | |
| 2017/0049587 A1 | 2/2017 | Herr et al. | |
| 2017/0071812 A1* | 3/2017 | Sandler | A61H 1/0274 |
| 2017/0202725 A1 | 7/2017 | Robertson et al. | |
| 2017/0246068 A1 | 8/2017 | Schultz et al. | |
| 2017/0259157 A1 | 9/2017 | Stewart et al. | |
| 2017/0279126 A1 | 9/2017 | Dreher | |
| 2017/0282360 A1 | 10/2017 | Telleria et al. | |
| 2017/0356201 A1 | 12/2017 | Campbell | |
| 2018/0028806 A1 | 2/2018 | Hardt et al. | |
| 2018/0042803 A1 | 2/2018 | Amundson | |
| 2018/0056104 A1 | 3/2018 | Cromie et al. | |
| 2018/0071129 A1 | 3/2018 | Ozsecen et al. | |
| 2018/0079071 A1 | 3/2018 | Griffith et al. | |
| 2018/0085280 A1 | 3/2018 | Shimada et al. | |
| 2018/0086178 A1 | 3/2018 | Stanek et al. | |
| 2018/0090961 A1 | 3/2018 | Namolovan et al. | |
| 2018/0092536 A1 | 4/2018 | Sandler et al. | |
| 2018/0116852 A1 | 5/2018 | Petursson et al. | |
| 2018/0125152 A1 | 5/2018 | Bruel | |
| 2018/0200878 A1 | 7/2018 | Tsai et al. | |
| 2018/0221237 A1 | 8/2018 | Swift et al. | |
| 2018/0235830 A1 | 8/2018 | Rokosz et al. | |
| 2018/0264642 A1 | 9/2018 | Harding et al. | |
| 2018/0283744 A1 | 10/2018 | Lynn et al. | |
| 2018/0290009 A1 | 10/2018 | Avila | |
| 2018/0296424 A1 | 10/2018 | Parra et al. | |
| 2018/0296425 A1 | 10/2018 | Lamb et al. | |
| 2018/0325765 A1 | 11/2018 | Wilmington | |
| 2019/0015233 A1 | 1/2019 | Galloway et al. | |
| 2019/0029918 A1 | 1/2019 | Nada et al. | |
| 2019/0060156 A1 | 2/2019 | Swift et al. | |
| 2019/0060157 A1 | 2/2019 | Lamb et al. | |
| 2019/0090744 A1 | 3/2019 | Mahfouz | |
| 2019/0105189 A1 | 4/2019 | Petursson et al. | |
| 2019/0105215 A1 | 4/2019 | Dalley et al. | |
| 2019/0159954 A1 | 5/2019 | Ozsecen et al. | |
| 2019/0168398 A1 | 6/2019 | Lessing et al. | |
| 2019/0224922 A1 | 7/2019 | Brensinger | |
| 2019/0240103 A1 | 8/2019 | Hepler et al. | |
| 2019/0280266 A1 | 9/2019 | Zhang et al. | |
| 2019/0283235 A1 | 9/2019 | Nam et al. | |
| 2019/0290464 A1 | 9/2019 | Fleming | |
| 2019/0290465 A1 | 9/2019 | Fleming | |
| 2019/0293223 A1 | 9/2019 | Free et al. | |
| 2019/0307583 A1 | 10/2019 | Herr et al. | |
| 2019/0328604 A1 | 10/2019 | Contreras-Vidal et al. | |
| 2019/0344433 A1 | 11/2019 | Lerner | |
| 2019/0350735 A1 | 11/2019 | Ingimundarson et al. | |
| 2019/0383313 A1 | 12/2019 | Fowler et al. | |
| 2020/0069441 A1 | 3/2020 | Larose et al. | |
| 2020/0100978 A1 | 4/2020 | Moody | |
| 2020/0114588 A1 | 4/2020 | Wang et al. | |
| 2020/0197209 A1 | 6/2020 | Bejarano et al. | |
| 2020/0206899 A1 | 7/2020 | Storz et al. | |
| 2020/0223071 A1 | 7/2020 | Mahoney et al. | |
| 2020/0253808 A1 | 8/2020 | Swift et al. | |
| 2020/0253822 A1 | 8/2020 | Sibue et al. | |
| 2020/0306070 A1 | 10/2020 | Hsu et al. | |
| 2020/0397641 A1 | 12/2020 | Teng et al. | |
| 2021/0177686 A1 | 6/2021 | Lamson et al. | |
| 2021/0251518 A1 | 8/2021 | Huizenga | |
| 2021/0369539 A1 | 12/2021 | Campbell et al. | |
| 2021/0369540 A1 | 12/2021 | Kemper et al. | |
| 2021/0369541 A1 | 12/2021 | Stuart et al. | |
| 2021/0369542 A1 | 12/2021 | Stuart et al. | |
| 2021/0370493 A1 | 12/2021 | Samia et al. | |
| 2021/0370494 A1 | 12/2021 | Hurley et al. | |
| 2021/0370495 A1 | 12/2021 | Swartz et al. | |

(56) References Cited

U.S. PATENT DOCUMENTS

| | | |
|---|---|---|
| 2021/0370496 A1 | 12/2021 | Stuart et al. |
| 2022/0015490 A1 | 1/2022 | Drasler |
| 2022/0087833 A1 | 3/2022 | Farris |
| 2022/0407129 A1 | 12/2022 | Phares |
| 2023/0055998 A1 | 2/2023 | Park et al. |

FOREIGN PATENT DOCUMENTS

| | | |
|---|---|---|
| CN | 103412003 A | 11/2013 |
| CN | 104582668 A | 4/2015 |
| CN | 105205436 A | 12/2015 |
| CN | 204814712 U | 12/2015 |
| CN | 105264255 A | 1/2016 |
| CN | 105590409 A | 5/2016 |
| CN | 105816301 A | 8/2016 |
| CN | 105992554 A | 10/2016 |
| CN | 106029039 A | 10/2016 |
| CN | 106137489 A | 11/2016 |
| CN | 106413998 A | 2/2017 |
| CN | 106420279 A | 2/2017 |
| CN | 110545777 A | 12/2019 |
| CN | 110868964 A | 3/2020 |
| CN | 111135031 A | 5/2020 |
| CN | 111571568 A | 8/2020 |
| DE | 102011107580 A1 | 1/2013 |
| EP | 2827809 A1 | 1/2015 |
| EP | 3173191 A2 | 5/2017 |
| EP | 3539528 A1 | 9/2019 |
| EP | 3576707 A4 | 3/2021 |
| FR | 1463850 A | 7/1966 |
| IN | 111278398 A | 6/2020 |
| JP | 1987501723 A | 7/1987 |
| JP | S62501723 A | 7/1987 |
| JP | 1988199965 A | 8/1988 |
| JP | S63199965 A | 8/1988 |
| JP | H07163607 A | 6/1995 |
| JP | 2000051289 A | 2/2000 |
| JP | 2005118959 A | 5/2005 |
| JP | 2006000347 A | 1/2006 |
| JP | 2007282991 A | 11/2007 |
| JP | 2010263934 A | 11/2010 |
| JP | 2011058564 A | 3/2011 |
| JP | 2011173211 A | 9/2011 |
| JP | 2012501739 A | 1/2012 |
| JP | 3179088 U | 10/2012 |
| JP | 2012532001 | 12/2012 |
| JP | 2014023773 A | 2/2014 |
| JP | 2015008938 A | 1/2015 |
| JP | 2015089386 A | 5/2015 |
| JP | 2015139665 A | 8/2015 |
| JP | 2016521212 A | 7/2016 |
| JP | 2016137146 A | 8/2016 |
| JP | 2017086296 A | 5/2017 |
| JP | 2018019899 A | 2/2018 |
| JP | 2018184266 A | 11/2018 |
| JP | 2019500928 A | 1/2019 |
| JP | 2019077037 A | 5/2019 |
| JP | 2019093464 A | 6/2019 |
| JP | 2019111635 A | 7/2019 |
| JP | 2020506030 A | 2/2020 |
| JP | 2020518295 A | 6/2020 |
| JP | 6860743 B2 | 4/2021 |
| KR | 10-2008-0048450 A | 6/2008 |
| KR | 10-2011-0104781 A | 9/2011 |
| KR | 10-2012-0025571 A | 3/2012 |
| KR | 10-2014-0062931 A | 5/2014 |
| KR | 20160020780 A | 2/2016 |
| KR | 101812603 B1 | 12/2017 |
| KR | 10-2020-0052323 A | 5/2020 |
| KR | 10-2020-0144460 A | 12/2020 |
| KR | 10-2021-0033449 A | 3/2021 |
| SU | 251758 | 11/1970 |
| WO | 8603816 A1 | 7/1986 |
| WO | 9722782 A1 | 6/1997 |
| WO | 0004852 A1 | 2/2000 |
| WO | 2008129096 A1 | 10/2008 |
| WO | 2009081710 A1 | 7/2009 |
| WO | 2010124172 A2 | 10/2010 |
| WO | 2011007569 A1 | 1/2011 |
| WO | 2011043095 A1 | 4/2011 |
| WO | 2012124853 A1 | 9/2012 |
| WO | 2013142777 A1 | 9/2013 |
| WO | 2013152929 A1 | 10/2013 |
| WO | 2014194257 A1 | 12/2014 |
| WO | 2015080596 A1 | 6/2015 |
| WO | 2015104832 A1 | 7/2015 |
| WO | 2016147195 A1 | 9/2016 |
| WO | 2016166442 A1 | 10/2016 |
| WO | 2016166588 A1 | 10/2016 |
| WO | 2016171548 A1 | 10/2016 |
| WO | 2016207855 A1 | 12/2016 |
| WO | 2017110453 A1 | 6/2017 |
| WO | 2018144937 A1 | 8/2018 |
| WO | 2018191710 A1 | 10/2018 |
| WO | 2018218336 A1 | 12/2018 |
| WO | 2018236225 A1 | 12/2018 |
| WO | 2019109178 A1 | 6/2019 |
| WO | 2019122364 A1 | 6/2019 |
| WO | 2019183397 A1 | 9/2019 |
| WO | 2019187030 A1 | 10/2019 |
| WO | 2020049886 A1 | 3/2020 |
| WO | 2021096874 A1 | 5/2021 |
| WO | 2021119512 A1 | 6/2021 |
| WO | 2021242742 A1 | 12/2021 |

OTHER PUBLICATIONS

Chinese Patent Office Second Office Action and Supplementary Search Report dated Mar. 30, 2022; Application No. 201880024598; 15 pages.
Chinese Patent Office Second Office Action dated Jul. 13, 2022; Application No. 201880056518.3; 6 pages.
Chinese Patent Office Supplemental Search Report dated Jul. 4, 2022, Application No. 201880056518.3, 4 pages.
European Patent Office Communication under Rule 71(3) EPC dated Apr. 19, 2022, Application No. 18 850 236.3, 46 pages.
European Patent Office Communication Under Rule 71(3) EPC, Application No. 18 783 814.9 dated Aug. 11, 2022, 44 pages.
European Patent Office Extended Search Report dated Oct. 18, 2022, Patent Application No. 22181044.3-1122, 7 pages.
Israel Notice of Deficiencies for Patent Application 269860 dated Jul. 25, 2022, 5 pages.
Israel Notice of Deficiencies for Patent Application No. 269860 dated Jul. 25, 2022, 5 pages.
Japan Final Rejection of Application No. 2019-563328 dated Jul. 6, 2022, 2 pages.
Japan Patent Office, "Final Rejection" in Applicaiton No. 2019-563328, Sep. 9, 2022, 4 pages.
Japanese IPO Final Rejection of Application No. 2019-563328, Aug. 9, 2022, 2 pages.
Japanese IPO Notification of Reason for Rejection of Application No. 2020-512042, Jun. 27, 2022, 2 pages.
National Intellectual Property Administration, P. R. China, "2nd Office Action" in Application No. 201880023218.5, Apr. 25, 2022, 15 pages.
Notification of Grant of Chinese Patent Application No. 201880056709 dated May 18, 2022, 2 pages.
Chinese Patent Office Decision on Rejection dated Oct. 10, 2022; Application No. 201880024597; 11 pages.
Chinese Patent Office Notification to Grant Patent Right for Invention dated Nov. 4, 2022; Application No. 201880056518.3; 2 pages.
Chinese Patent Office Third Office Action dated Oct. 20, 2022; Application No. 201880023218.5; 8 pages.
European Patent Office Communication under Rule 71(3) EPC dated Nov. 29, 2022, Application No. 18 783 814.9, 46 pages.
European Patent Office Intention to Grant, Application No. 18 783 814.9 dated Nov. 29, 2022, 83 pages.
International Search Report and Written Opinion mailed Dec. 1, 2022, Patent Application No. PCT/US2022/075098, 12 pages.

(56) References Cited

OTHER PUBLICATIONS

International Search Report and Written Opinion mailed Dec. 1, 2022, Patent Application No. PCT/US2022/075099, 12 pages.
International Search Report and Written Opinion mailed Dec. 5, 2022, Patent Application No. PCT/US2022/075097, 11 pages.
International Search Report and Written Opinion mailed Dec. 6, 2022, Patent Application No. PCT/US2022/075095, 10 pages.
International Search Report and Written Opinion mailed Nov. 29, 2022, International Patent Application No. PCT/US2022/075094, filed Aug. 17, 2022, 11 pages.
International Search Report and Written Opinion mailed Nov. 29, 2022, International Patent Application No. PCT/US2022/075096, filed Aug. 17, 2022, 11 pages.
Israel Notice of Acceptance for Patent Application No. 272621 dated Dec. 22, 2022, 4 pages.
Israel Notice of Deficiencies for Patent Application No. 272623 dated Dec. 7, 2022, 4 pages.
Israel Notice of Deficiencies for Patent Application No. 282165 dated Dec. 18, 2022, 4 pages.
Japan Decision to Grant Application No. 2020-512042 dated Jan. 13, 2023, 2 pages.
Japan Final Office Action and Decision to Reject Amendment of Application No. 2019-554877 dated Nov. 7, 2022, 4 pages.
International Search Report and Written Opinion mailed Jul. 18, 2016, International Patent Application No. PCT/US2016/024366, filed Mar. 25, 2016, 7 pages.
Taniguchi, "Flexible Artificial Muscle Actuator Using Coiled Shape 5 Memory Alloy Wires," APCBEE Procedia 7:54-59, Jan. 1, 2013.
International Search Report and Written Opinion mailed Jul. 19, 2018, International Patent Application No. PCT/US2018/027643, filed Apr. 13, 2018, 7 pages.
International Search Report and Written Opinion mailed Apr. 26, 2018, International Patent Application No. PCT/US2018/016729, filed Feb. 2, 2018, 7 pages.
Tamez-Duque et al., "Real-time strap pressure sensor system for powered exoskeletons," Sensors 15(2):4550-4563. Feb. 2015.
International Search Report and Written Opinion mailed Dec. 6, 2018, Patent Application No. PCT/US2018/048639, 7 pages.
International Search Report and Written Opinion mailed Dec. 6, 2018, International Patent Application No. PCT/US2018/048638, filed Aug. 29, 2018, 8 pages.
International Search Report and Written Opinion mailed Mar. 30, 2021, Patent Application No. PCT/US2020/064647, 10 pages.
International Search Report and Written Opinion mailed Jun. 3, 2021, Patent Application No. PCT/US2021/019711, 12 pages.
Huang et al., "Interactive learning for sensitivity factors of a human-powered augmentation lower exoskeleton," 2015 IEEE/RSJ International Conference on Intelligent Robots and Systems (IROS), Sep. 28, 2015, 7 pages.
International Search Report and Written Opinion mailed Aug. 26, 2021, Patent Application No. PCT/US2021/034447, 7 pages.
International Search Report and Writtent Opinion mailed Aug. 26, 2021, Patent Application No. PCT/US2021/034468, 8 pages.
International Search Report and Written Opinion mailed Sep. 2, 2021, Patent Application No. PCT/US2021/034450, 9 pages.
International Search Report and Written Opinion mailed Sep. 9, 2021, Patent Application No. PCT/US2021/034443, 8 pages.
International Search Report and Written Opinion mailed Aug. 26, 2021, Patent Application No. PCT/US2021/034444, 7 pages.
International Search Report and Written Opinion mailed Sep. 9, 2021, Patent Application No. PCT/US2021/034579, 8 pages.
International Search Report and Written Opinion mailed Aug. 26, 2021, Patent Application No. PCT/US2021/034593, 10 pages.
International Search Report and Written Opinion mailed Sep. 2, 2021, Patent Application No. PCT/US2021/034030, 9 pages.
USPTO Office Action in U.S. Appl. No. 16/862,400 dated Mar. 22, 2023, 13 pages.
USPTO Office Action in U.S. Appl. No. 17/119,825 dated May 23, 2023, 19 pages.
JSPTO Office Action in U.S. Appl. No. 17/558,481 dated Mar. 23, 2023, 49 pages.
Canadian IPO Office Action and Examination Search Report dated Mar. 21, 2023, 7 pages.
Chinese Patent Office First Office Action dated Jun. 16, 2023; Application No. 202111540872.3; 14 pages.
Chinese Patent Office Notification to Grant Patent Right for Invention dated Jul. 10, 2023; Application No. 201880024597.X; 2 pages.
USPTO Office Action in U.S. Appl. No. 16/838,347 dated Jun. 8, 2023, 5 pages.
Chinese Patent Office Fourth Office Action dated Mar. 31, 2023, Application No. 201880023218.5; 7 pages.
Japan First Office Action, Application No. 2022-072995 dated Mar. 8, 2023, 2 pages.
Branham, "3 Advantages of Using an Oval Bore Compact Cylinder," W.C. Branham Blog—Solutions in Motion TM. Retrieved Feb. 9, 2023, from https://blog.wcbranham.com/oval-bore-compact-cylinder, Jan. 12, 2018, 7 pages.
Chinese Patent Office Decision on Rejection dated Nov. 25, 2022; Application No. 201880024597; 11 pages.
Israel Notice of Acceptance for Patent Application No. 268306 dated Feb. 1, 2023, 3 pages.
European Patent Office Notice of Intention to Grant, Application No. 18748599.0, Aug. 16, 2023, 52 pages.
Japan PTO Rejection of Application No. 2019-563328 dated Jul. 13, 2023, 3 pages.
Chinese Patent Office Notification of Grant of Application No. 201880023218.5, Sep. 6, 2023, 2 pages.
European Patent Office Extended Search Report dated Jan. 29, 2024, Application No. 23196713.4, 7 pages.
European Patent Office Extended Search Report, Application No. 20899495.4 dated Jan. 18, 2024, 11 pages.
Israel Notice of Deficiencies for Patent Application 269860 dated Jan. 10, 2024, 4 pages.
Israel Notice of Deficiencies for Patent Application 269860 dated Nov. 14, 2023, 4 pages.
Japan First Office Action, Application No. 2022-535872 dated Feb. 15, 2024, 8 pages.
Japan Office Action, Application No. 2023-017338 dated Dec. 12, 2023, 2 pages.
Japan Office Action, Application No. 2023-034202 dated Jan. 9, 2024, 4 pages.
Japan PTO Rejection of Application No. 2022-573517 dated Jan. 9, 2024, 2 pages.
Japanese IPO Notification of Reason for Rejection of Application No. 2022-176048, Nov. 26, 2023, 5 pages.
Japanese IPO Notification of Reason for Rejection of Application No. 2022-573516, Jan. 15, 2024, 3 pages.
USPTO Non-Final Office Action in U.S. Appl. No. 17/327,121 dated Aug. 29, 2023, 8 pages.
USPTO Notice of Allowance in U.S. Appl. No. 17/119,830 dated Nov. 8, 2023, 9 pages.
USPTO Office Action in U.S. Appl. No. 16/827,484 dated Dec. 4, 2023, 18 pages.
USPTO Office Action in U.S. Appl. No. 16/838,347 dated Jan. 24, 2023, 7 pages.
USPTO Office Action in U.S. Appl. No. 17/185,754 dated Jan. 18, 2024, 16 pages.
USPTO Office Action in U.S. Appl. No. 17/332,172 dated Oct. 25, 2023, 39 pages.
USPTO Office Action in U.S. Appl. No. 17/332,507 dated Nov. 8, 2023, 23 pages.
USPTO Office Action in U.S. Appl. No. 17/332,818 dated Nov. 13, 2023, 29 pages.
USPTO Office Action in U.S. Appl. No. 17/558,481 dated Nov. 29, 2023, 17 pages.
Yoshikawa, "Human Interface Using Hand Movement Recognition Method Based on Myoelectricity," Next Generation Human Interface Development Frontier, Jun. 11, 2013, 14 pages.
USPTO Office Action dated Mar. 7, 2024, U.S. Appl. No. 17/119,825, 18 pages.
Japan Office Action, Application No. 2023-017338 dated Nov. 9, 2023, 4 pages.

(56) References Cited

OTHER PUBLICATIONS

USPTO Notice of Allowance of U.S. Appl. No. 17/729,934 dated Aug. 23, 2023, 22 pages.
USPTO Office Action in U.S. Appl. No. 17/327,121 dated Aug. 29, 2023, 8 pages.
Canadian IPO Notice of Allowance dated Mar. 19, 2024, Patent Application No. 3,051, 105, 1 page.
Chu, "Human-Expsystem Adaptation," MIT School of Engineering, Oct. 2018 [retrieved Apr. 25, 2024 from https://engineering.mit.edu/engage/engineering-in-action/human-exosystem-adaptation/,] 9 pages.
Dephy, "Build Faster A Safe Robotics Platform that Actually Works?" Retrieved Apr. 25, 2024 from https://web.archive.org/web/20221226232116/https://dephy.com/faster/, 11 pages.
European Patent Office Extended Search Report dated Apr. 8, 2024, Application No. 20899495.4, 10 pages.
Japan IPO Trial Decision Allowing Application No. 2019-554877 dated Apr. 1, 2024, 2 pages.
MIT School of Engineering, "Human-exosystem Adaptation," https://www.youtube.com/watch?v=GXGHi_n1uR0, Oct. 4, 2018, 2 pages.
University of Michigan, "Understanding Exoskeletons Use Motivation," 2020 [retrieved Apr. 25, 2024 from https://neurobionics.robotics.umich.edu/research/biomechanical-science/dephy-ankle-exoskeletons/,] 4 pages.
USPTO Office Action dated Apr. 4, 2024, U.S. Appl. No. 16/838,347, 7 pages.
Canadian Intellectual Property Office Office Action dated Dec. 6, 2024, Application No. 3,072,504, 6 pages.
Canadian IPO Office Action dated Dec. 5, 2024, Patent Application No. 3,072,622, 7 pages.
Canadian IPO Office Action dated Jun. 27, 2024 in Application No. 3,055,435, 5 pages.
Chinese Patent Office First Office Action dated Feb. 19, 2025; Application No. 202210922312.2; 43 pages.
Chinese Patent Office First Office Action dated Jan. 15, 2025; Application No. 202180040509.7; 3 pages.
Chinese Patent Office First Office Action dated Jan. 17, 2025, Application No. 202180045080.0; 10 pages.
Chinese Patent Office First Office Action dated Jan. 17, 2025; Application No. 202180045079.8; 10 pages.
Chinese Patent Office First Office Action dated Jan. 17, 2025; Application No. 202189945078.3; 13 pages.
Chinese Patent Office First Office Action dated Mar. 1, 2025; Application No. 202180045052.9; 74 pages.
Chinese Patent Office Notification of Grant of Application No. 20211150872.3, Nov. 19, 2024, 2 pages.
Chinese Patent Office Notification to Grant Patent Right for Invention dated Jul. 4, 2024; Application No. 2022-573514; 1 page.
Dephy, "Getting Started," retrieved May 28, 2024 from https://dephy.com/start/, 23 pages.
European Patent Office Exam Report dated Jan. 14, 2025, Application No. 22181044.3, 4 pages.
European Patent Office Extended Search Report dated Jun. 12, 2024, Application No. 21812817.1, 12 pages.
European Patent Office Extended Search Report dated Jun. 17, 2024, Application No. 21814117.4, 7 pages.
European Patent Office Extended Search Report dated Jun. 21, 2024, Patent Application No. 21812103.6, 12 pages.
European Patent Office Extended Search Report dated May 28, 2024, Application No. 21814414.5, 11 pages.
European Patent Office Extended Search Report, Application No. 21812695.1 dated Jun. 18, 2024, 10 pages.
European Patent Office Extended Search Report, Application No. 21812992.2 dated Jun. 21, 2024, 11 pages.
European Patent Office Notice of Intention to Grant, Application No. 20899495.4, dated Feb. 27, 2025, 73 pages.
European Patent Office Notice of Intention to Grant, Application No. 20899495.4, Feb. 27, 2025, 73 pages.
Israel Notice of Acceptance dated Apr. 1, 2024, Patent Application No. 272623, 3 pages.
Israel Notice of Deficiencies for Patent Application 293829 dated Dec. 9, 2024, 5 pages.
Japan Decision to Grant Application No. 2022-176048 dated Nov. 14, 2024, 2 pages.
Japan Decision to Grant Application No. 2022-573509 dated Aug. 22, 2024, 2 pages.
Japan IPO Office Action dated Aug. 13, 2024, Application No. 2022-176048, 2 pages.
Japan Notice of Patent Grant, Application No. 2022-573519 dated Aug. 8, 2024, 1 page.
Japan Office Action, Application No. 2023-017338 dated Aug. 26, 2024, 3 pages.
Japan Patent Office, "Decision to Grant" in application No. 2022-573515, Sep. 30, 2024, 1page.
Japan Patent Office, "Decision to Grant" in application No. 2022-573516, Sep. 19, 2024, 1page.
Japan Trial Decision Notice of Patentability of Application No. 2019-563328 dated Aug. 13, 2024, 2 pages.
Khalili, et al., "Studies on Practical Applications of Safe-Fall Control Strategies for Lower Limb Exoskeletons*," 2019 IEEE 16th INternational Conference on Rehabilitation Robotics, Jan. 24-28, 2019, 6 pages.
USPTO Final Office Action dated Aug. 14, 2024, U.S. Appl. No. 17/332,507, 29 pages.
USPTO Final Office Action dated Sep. 25, 2024, U.S. Appl. No. 17/119,825, 24 pages.
USPTO Notice of Allowance in U.S. Appl. No. 17/119,825 dated Feb. 10, 2025, 8 pages.
USPTO Notice of Allowance of U.S. Appl. No. 17/889,750 dated Jun. 11, 2024, 9 pages.
USPTO Office Action dated Aug. 14, 2024, U.S. Appl. No. 17/332,818, 35 pages.
USPTO Office Action Dated Aug. 28, 2024, U.S. Appl. No. 17/331,956, 21 pages.
USPTO Office Action dated Jan. 23, 2025, U.S. Appl. No. 17/331,961, 25 pages.
USPTO Office Action dated Jul. 31, 2024, U.S. Appl. No. 17/331,961, 20 pages.
USPTO Office Action dated Jun. 14, 2024, U.S. Appl. No. 17/558,481, 15 pages.
USPTO Office Action in U.S. Appl. No. 17/327,121 dated Feb. 11, 2025, 8 pages.
USPTO Office Action in U.S. Appl. No. 17/329,632 dated Aug. 19, 2024, 20 pages.
USPTO Office Action in U.S. Appl. No. 17/332,172 dated Dec. 17, 2024, 39 pages.
USPTO Office Action in U.S. Appl. No. 17/332,507 dated Feb. 11, 2024, 26 pages.
USPTO Office Action in U.S. Appl. No. 17/332,818 dated Feb. 14, 2025, 28 pages.
USPTO Office Action in U.S. Appl. No. 17/558,481 dated Dec. 20, 2024, 12 pages.
European Patent Office Notice of Intention to Grant, Application No. 18851608.2, Mar. 25, 2025, 56 pages.
Japan Office Action dated Feb. 3, 2025, Application No. 2023-017338, 2 pages.

* cited by examiner

EXOSKELETON DATA LABELING SYSTEM AND METHOD

CROSS-REFERENCE TO RELATED APPLICATIONS

This application is a continuation of U.S. patent application Ser. No. 15/887,866, filed Feb. 2, 2018, which is a non-provisional of and claims the benefit of U.S. Provisional Application No. 62/454,575, filed Feb. 3, 2017 entitled "SYSTEM AND METHOD FOR USER INTENT RECOGNITION," which application is hereby incorporated herein by reference in its entirety and for all purposes.

U.S. patent application Ser. No. 15/887,866 is also a non-provisional of and claims the benefit of U.S. Provisional Application No. 62/485,284, filed Apr. 13, 2017 entitled "SYSTEM AND METHOD FOR USER INTENT RECOGNITION," which application is hereby incorporated herein by reference in its entirety and for all purposes.

Figure 1:
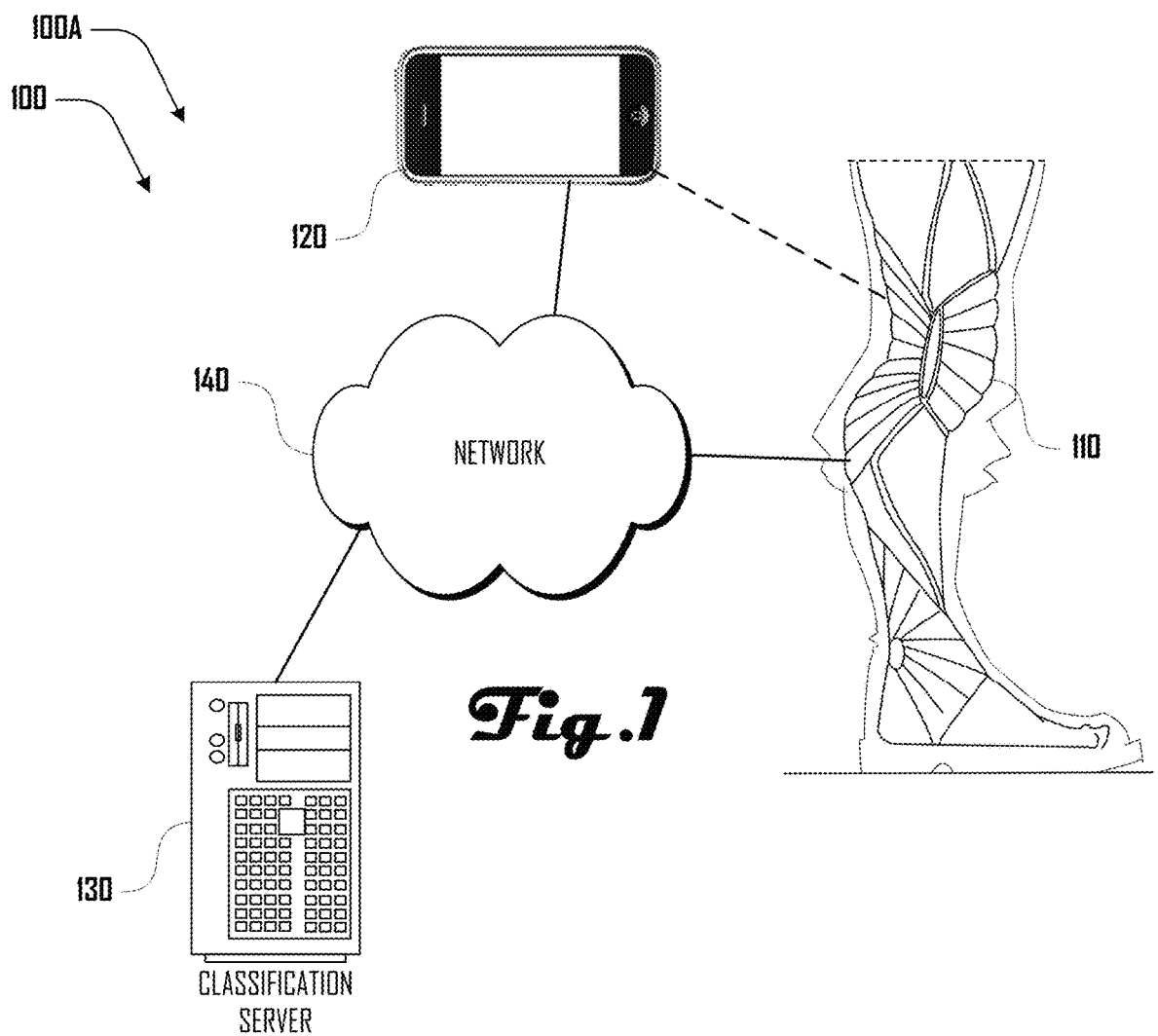
FIG. 1 is an exemplary diagram illustrating an embodiment of an exoskeleton network.

It should be noted that the figures are not drawn to scale and that elements of similar structures or functions are generally represented by like reference numerals for illustrative purposes throughout the figures. It also should be noted that the figures are only intended to facilitate the description of the preferred embodiments. The figures do not illustrate every aspect of the described embodiments and do not limit the scope of the present disclosure.

DETAILED DESCRIPTION

In one aspect, this application discloses example embodiments pertaining to the design of novel programs for the recognition of intent for users of one or more powered exoskeleton. Various embodiments described herein offer a substantial improvement over the intent recognition programs used in conventional devices. For example, a conventional method for intent recognition is the expert design of a finite state machine including designed transition guards that are ad hoc established by the developers to improve accuracy. In contrast, various example methods described herein allow intent recognition programs to adapt over time either based on learned performance or to adapt to the unique behavior of an individual operator. Various example methods described herein provide for intent recognition programs that are able to increase accuracy of recognition, reduce delay of recognition, and customize the performance for each user. Accordingly, various embodiments relate to methods that can be performed automatically, without human interaction, or with only minimal human interaction at limited specific desirable times as described herein.

Turning to FIG. 1, an example exoskeleton device network 100 of a first embodiment 100A is illustrated, which includes an exoskeleton system 110, a user device 120 and a classification server 130, which are operably connected via a network 140. Additionally, the exoskeleton system 110 and user device 120 are shown being directly operably connected.

In various embodiments described in more detail herein, an exoskeleton system 110 can be configured to communicate with a local user device 120, which can act as an input device, display, and/or user interface for the exoskeleton system 110. For example, the user device 120 can present information about various states of exoskeleton system 110 and the user device 120 can be used to control the exoskeleton system 110, including providing input related to state classification as discussed herein.

In the example of FIG. 1, the exoskeleton system 110 and user device 120 are shown being directly operably connected via a wireless communication channel (e.g., Bluetooth) and indirectly via the network 140, which can include one or more wired and/or wireless network including the Internet, a Wi-Fi network, a cellular network, a local area network (LAN), wide area network (WAN), or the like. However, in some embodiments, one of these operable connections can be absent. For example, in one embodiment, the exoskeleton system 110 can be configured to communicate with the user device 120 only via a direct local connection and not via the network 140. In another embodiment, the exoskeleton system 110 can be configured to only communicate via local communication channels with the user device 120, but unable to communicate with devices such as the classification server 130 or user device 120 via the network 140. In some examples, however, the exoskeleton system 110 can communicate with devices such as the classification server 130 via the user device 120.

In some embodiments, the classification server 130 can comprise one or more devices configured with various capabilities, which are described in more detail herein. While a physical server is shown in the example of FIG. 1, in further embodiments, the classification server 130 can comprise one or more virtual or non-virtual servers, or the like. In some examples, the classification server 130 can be absent.

Although the user device 120 in the example exoskeleton network 100 is shown as a smartphone, in further embodiments, various other suitable devices can comprise the user device 120, including a tablet computer, smart watch, laptop computer, desktop computer, gaming device, entertainment device, home automation device, embedded system, or the like. Additionally, in some examples, the user device 120 can be an integral part of the exoskeleton system 110. In other words, in some examples, user device 120 and exoskeleton system 110 can be combined. Additionally, in some embodiments, the user device 120 can be absent or present in any suitable plurality.

Figure 2:
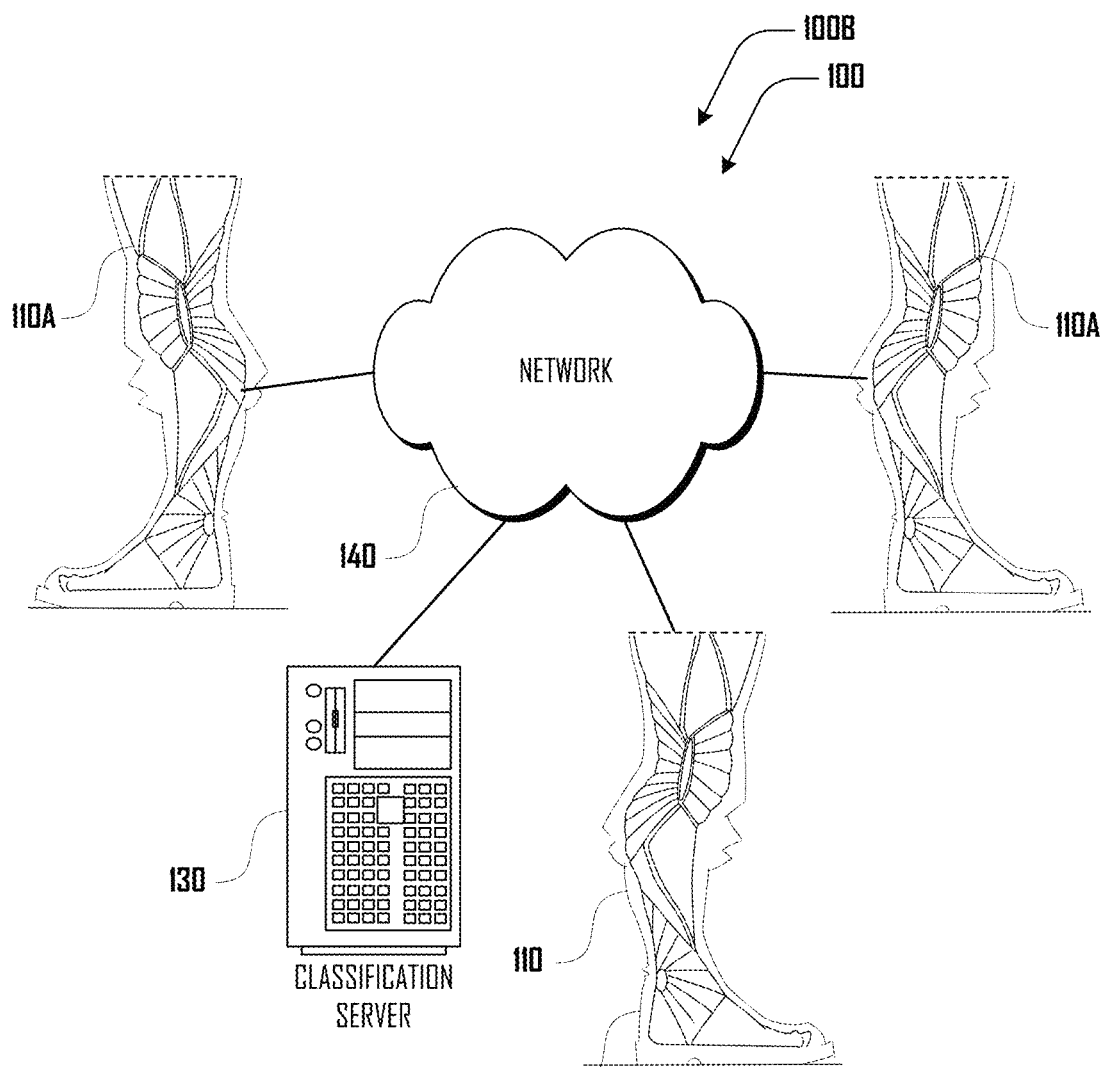
FIG. 2 is an exemplary diagram illustrating another embodiment of an exoskeleton network.

As described in more detail herein, the exoskeleton system 110 can be any suitable exoskeleton system having various capabilities. According, the example leg exoskeleton system 110 shown in FIG. 1 should not be construed as being limiting on the wide variety of exoskeleton systems that are within the scope and spirit of the present disclosure. Additionally, in some embodiments, an exoskeleton network 100 can comprise a plurality of exoskeleton systems 110. For example, FIG. 2 illustrates another embodiment 100B of an exoskeleton network 100 that comprises a plurality of exoskeleton systems 110A, 110B, 110C and a classification server 130.

Figure 3:
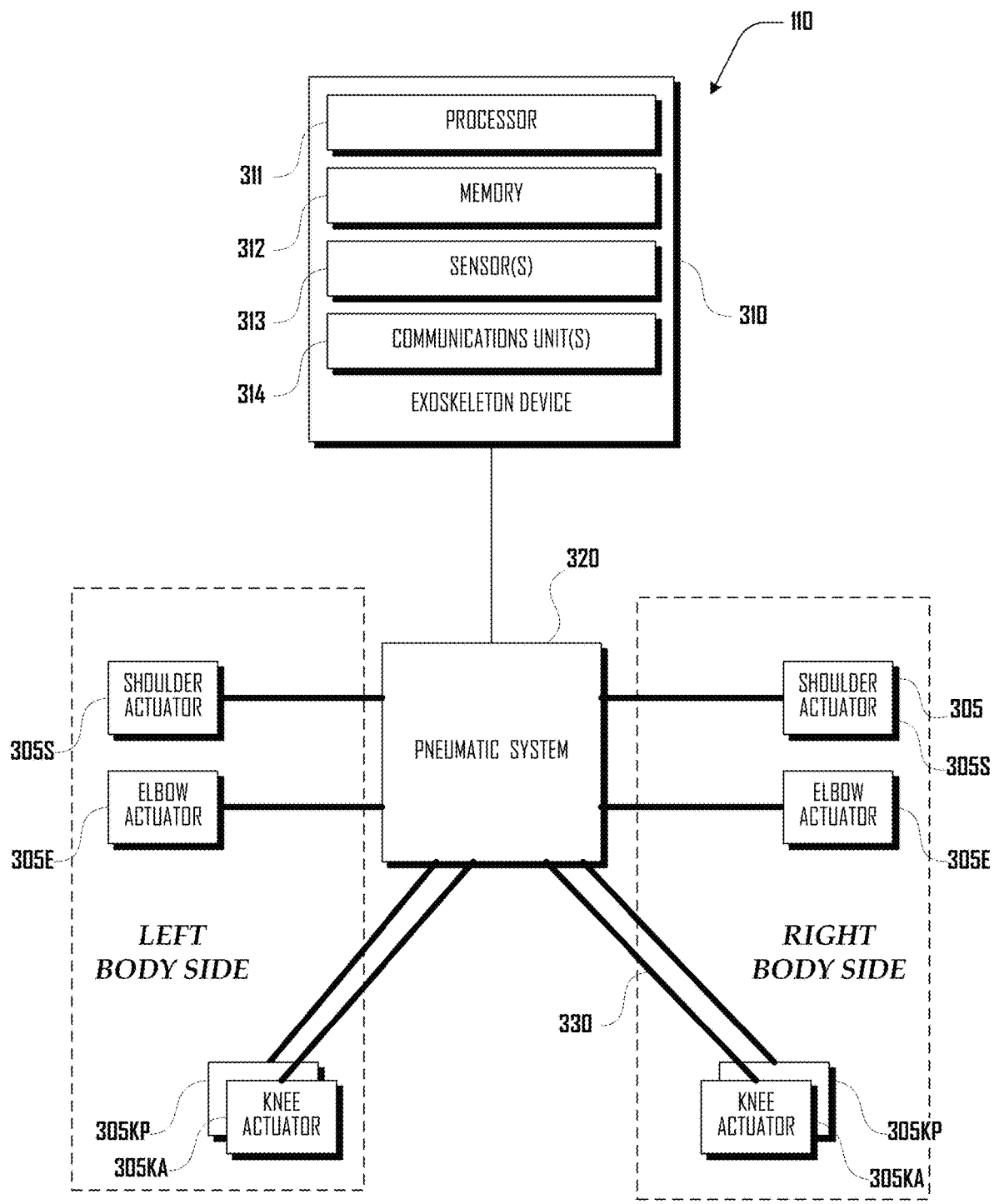
FIG. 3 is an exemplary block diagram illustrating an embodiment of an exoskeleton system.
Figure 10:
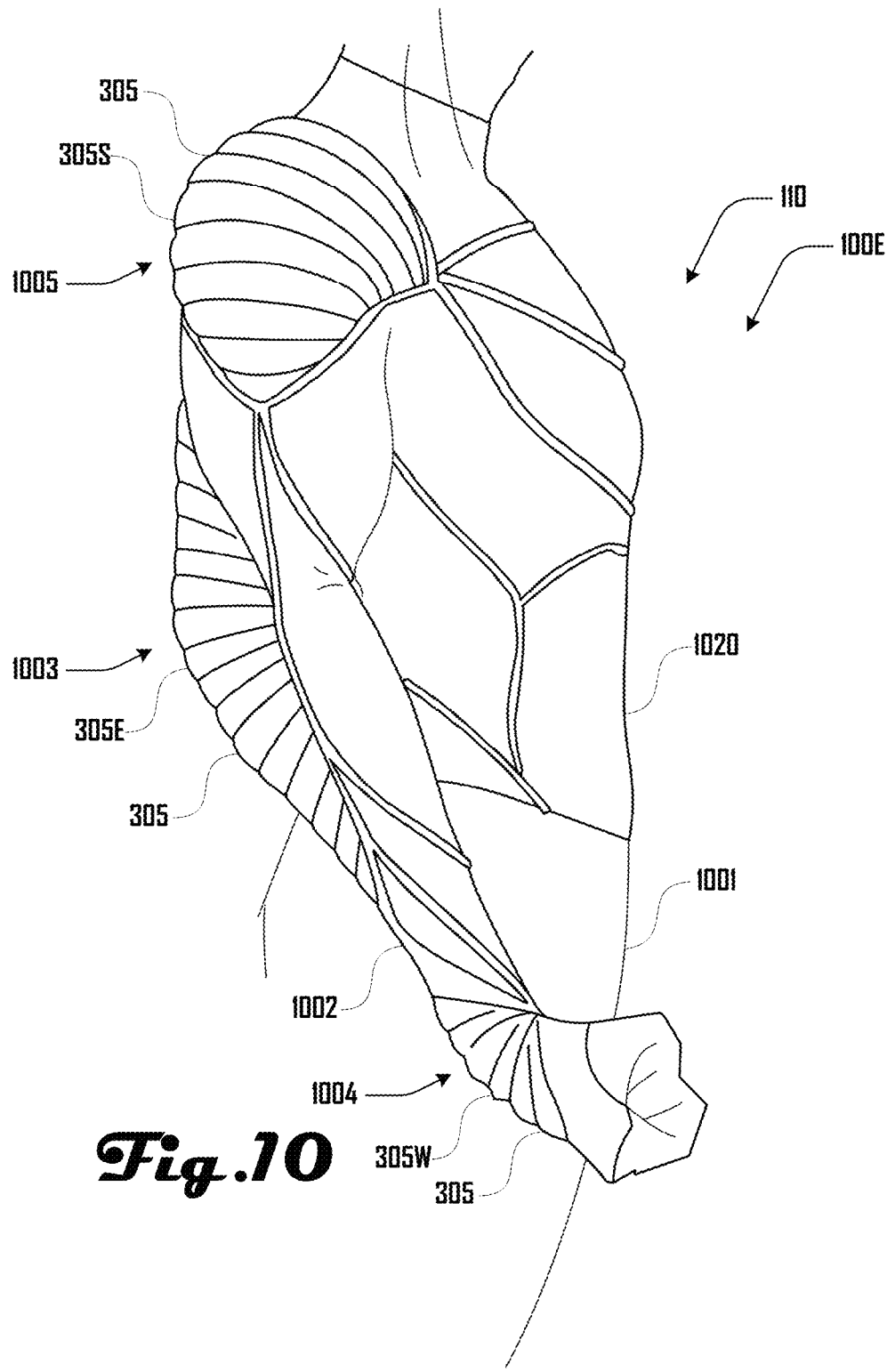
FIG. 10 is an exemplary illustration of an embodiment of an exoskeleton system.
Figure 11:
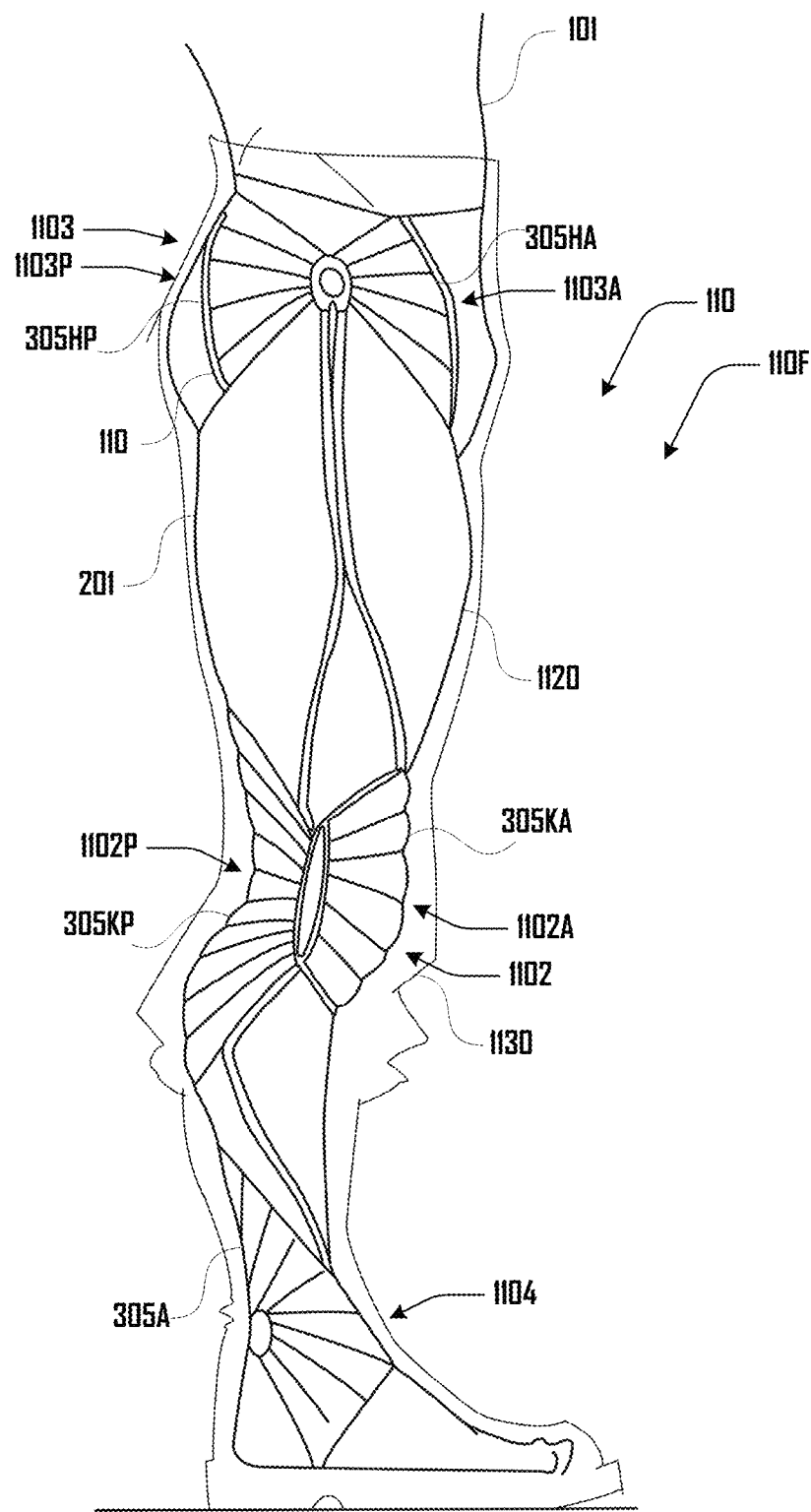
FIG. 11 is an exemplary illustration of another embodiment of an exoskeleton system.

FIG. 3 is a block diagram of an example embodiment 110D of an exomuscle system 110 that includes an exoskeleton device 310 that is operably connected to a pneumatic system 320. The exoskeleton device 310 comprises a processor 311, a memory 312, one or more sensors 313 and a communication unit 314. A plurality of actuators 305 are operably coupled to the pneumatic system 320 via respective pneumatic lines 330. The plurality of actuators 305 include pairs of shoulder-actuators 305S, elbow-actuators 305E, anterior knee-actuators 305KA, and posterior knee-actuators 305KP that are positioned on the right and left side of a body. For example, as discussed above, the example exomuscle system 110D shown in FIG. 3 can be part of top and/or bottom suits 110E, 110F (e.g., as shown in FIGS. 10 and 11), with the actuators 305 positioned on respective parts of the body as discussed herein. For example, the shoulder-actuators 305S can be positioned on left and right shoulders; elbow-actuators 305E can be positioned on left and right elbows; and anterior and posterior knee-actuators 305KA, 305KP can be positioned on the knee anterior and posterior.

In various embodiments, the example system 110D can be configured to move and/or enhance movement of the user wearing the exomuscle system 110D. For example, the exoskeleton device 310 can provide instructions to the pneumatic system 320, which can selectively inflate and/or deflate the actuators 305. Such selective inflation and/or deflation of the actuators 305 can move the body to generate and/or augment body motions such as walking, running, jumping, climbing, lifting, throwing, squatting, or the like.

In some embodiments, such movements can be controlled and/or programmed by the user that is wearing the exomuscle system 110D or by another person. In some embodiments, the exomuscle system 110D can be controlled by movement of the user. For example, the exoskeleton device 310 can sense that the user is walking and carrying a load and can provided a powered assist to the user via the actuators 305 to reduce the exertion associated with the load and walking. Accordingly, in various embodiments, the exomuscle system 110D can react automatically without direct user interaction. In further embodiments, movements can be controlled in real-time by a controller, joystick or thought control. Additionally, various movements can pre-preprogrammed and selectively triggered (e.g., walk forward, sit, crouch) instead of being completely controlled. In some embodiments, movements can be controlled by generalized instructions (e.g. walk from point A to point B, pick up box from shelf A and move to shelf B).

In various embodiments, the exoskeleton device 310 can be operable to perform methods or portions of methods described in more detail below, including methods 400, 500, 600, 700, 800 and the like. For example, the memory 312 can include non-transient computer readable instructions, which if executed by the processor 311, can cause the exoskeleton system 110 to perform methods or portions of methods described herein. The communication unit 314 can include hardware and/or software that allows the exoskeleton system 110 to communicate with other devices, including a user device 120, classification server 130, other exoskeleton systems 110, or the like, directly or via a network (see, e.g., FIGS. 1 and 2).

In some embodiments, the sensors 313 can include any suitable type of sensor, and the sensors 313 can be located at a central location or can be distributed about the exomuscle system 110D. For example, in some embodiments, the system exoskeleton system 110D can comprise a plurality of accelerometers, force sensors, position sensors, and the like, at various suitable positions, including at the actuators 305 or any other body location. Accordingly, in some examples, sensor data can correspond to a physical state of one or more actuators 305, a physical state of a portion of the exoskeleton system 110, a physical state of a portion of the exoskeleton system 110 generally, and the like. In some embodiments, the exoskeleton system 110D can include a global positioning system (GPS), camera, range sensing system, environmental sensors, or the like.

The pneumatic system 320 can comprise any suitable device or system that is operable to inflate and/or deflate the actuators 305. For example, in one embodiment, the pneumatic system can comprise a diaphragm compressor as disclosed in co-pending related patent application Ser. No. 14/577,817 filed Dec. 19, 2014, which claims the benefit of U.S. Provisional Application No. 61/918,578, filed Dec. 19, 2013.

Figure 12:
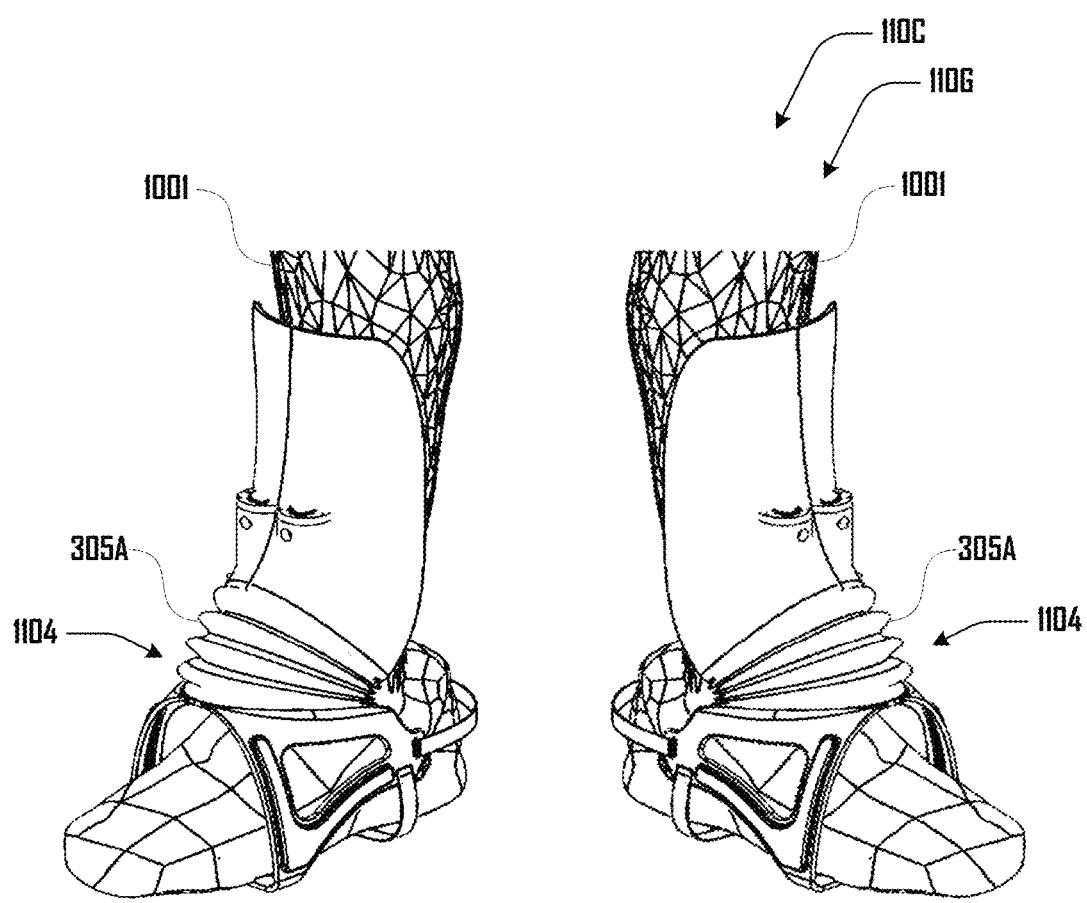
FIG. 12 is an exemplary illustration of a further embodiment of an exoskeleton system.

As discussed herein, various suitable exoskeleton systems 110 can be used with the example systems and methods discussed herein, including exoskeleton systems 110 of FIGS. 10, 11 and 12, as described herein. However, such examples should not be construed to be limiting on the wide variety of exoskeleton systems 110 or portions thereof that are within the scope and spirit of the present disclosure. Accordingly, exoskeleton systems 110 that are more or less complex than the examples of FIGS. 3, 10, 11 and 12 are within the scope of the present disclosure.

Additionally, while various examples relate to an exoskeleton system 110 associated with the legs or lower body of a user, further examples can related to any suitable portion of a user body including the torso, arms, head, legs, or the like. Also, while various examples relate to exoskeletons, it should be clear that the present disclosure can be applied to other similar types of technology, including prosthetics, body implants, robots, or the like. Further, while some examples can relate to human users, other examples can relate to animal users, robot users, or the like.

The present disclosure includes various methods for developing example embodiments of a data driven intent recognition program for exoskeleton applications. Various preferred embodiments include an intent recognition system that uses data collected from the sensors 313 included in one or more exoskeleton system 110 in order to allow for unsupervised refinement of the intent recognition performance.

For example, data driven intent recognition program can comprise a classifier or other program that is processing sensor data (e.g., data received from one or more sensor 313) up to a point in time (t=0) to determine the intended maneuver of the user at that time. In other words, the exoskeleton system 110 can run a program that anticipates intended actions by a user wearing the exoskeleton system 110, based at least in part on received sensor data.

In some examples, a source of error for such programs or methods can be related to the ability of the real-time classifiers to deliver accurate predictions of the user's motions, in some cases before the operator has made significant physical motions to act on their intent. For example, if these programs are looking to identify the toe-off phase of the gait of a user wearing the exoskeleton system 110, the intent recognition program can seek to find an intent for the toe-off phase when only having sensor data contained within the following set $t=[-n:0]$, given that sensors 313 cannot detect behaviors that have not yet occurred.

In various examples, a theoretically ideal program would be able to detect toe-off as soon as all ground contact signals at the foot go to zero. However, in a some systems, the program may have to compete with a variety of imperfections such as sensor noise, and the like, that mean the exoskeleton system 110 cannot respond to the signal the moment the ground contact signals drop to zero and in many cases would need to wait for the sensor data to repeatedly indicate ground contact has ended.

This can result in a delay to the speed of the classification behavior of such classification programs. As a result, some data driven intent recognition program incorporate supervision where an expert is able to parse the sensor data and indicate truth with the context of full sensor data such that the data driven methods can train themselves to best approximate the selections of the supervisory expert.

The present disclosure describes some example methods that can remove the need for an expert supervisor. Specifically, the behavior of classification methods can be significantly improved in some examples if the classifications were being completed on sensor data for time leading up to and after the specific time of interest, $t=[-n:n]$. Accordingly, various embodiments discussed herein are directed to methods that focus on classification behavior.

Some example methods can reconsider the classification of a maneuver by a user of exoskeleton system 110 a set time in the past (consider $t=-n$), which can allow the classification program to use data from sensors 313 from before and after the maneuver by a user of exoskeleton system 110 in question which comprise times $t=[-2n:0]$. In some embodiments, classification via such a method can be completed much more accurately than a program that is responsible for instantaneously classifying maneuvers of a user of exoskeleton system 110. Accordingly, various example methods can use sensor data to refine the instantaneous prediction that would have taken place at $t=-n$, in an effort to make the exoskeleton system 110 perform more like the assumed truth data that is determined from the foresight classification.

In one embodiment, a process of comparing and updating instantaneous classification can happen on an off-board computer (e.g., a user device 120, classification server 130, or the like) and then refined classifier data can be redeployed onto one or more exoskeleton systems 110 in order to improve the performance of the one or more exoskeleton systems 110. In such an embodiment, pertinent sensor data can be streamed off the exoskeleton system 110 and processed on the classification server 130 where an updated or improved classification method can be generated. The resulting classification method data can be deployed to the exoskeleton device 110 to allow it to execute the refined intent recognition behavior embodied in the classification method data. However, in further embodiments, such processing can occur on one or more other suitable devices, including at the exoskeleton device 310 or at the user device 120 (e.g., a smartphone, a laptop computer, a server or other suitable device).

Some embodiments of this example method can provide high frequency updates of a classification program as fast as every control loop, while others can have significantly slower update cycles such as embodiments that only update the classification program once a year. Still others can update the classification program in non-periodic intervals based on other rules such as an embodiment that updates the local classification program of a exoskeleton system 110 when it is determined that the update will improve accuracy by 1% or other suitable amount or metric.

In some examples of adaptive exoskeleton systems 110 that are used in conjunction with human users, it can be important to be aware of the speed that the adaptive intent recognition is adapting. Specifically, if the adaptive exoskeleton system 110 adapts too fast, it could respond to intermittent atypical behaviors that are not representative of the user's typical motions. If the exoskeleton system 110 adapts a slight amount slower, it can be possible in some embodiments to create an adaptive exoskeleton system 110 that responds at a similar bandwidth to the user's own internal learning process associated with the user learning how to use the exoskeleton system 110. Where such tuned adaption speed is implemented, in some embodiments the exoskeleton system 110 can begin adapting its behaviors just as the user is beginning to trust how the exoskeleton system 110 works, leading to a new learning phase for the user.

As a result, it can be important in some examples for adaptive intent recognition programs to adapt at a speed significantly different than that of the users own internal adaptations. In many embodiments, this can be addressed by making the exoskeleton system 110 adapt at a speed significantly slower than that of the user. In other embodiments, the adaptation speed of an intent recognition program can be user-selectable to allow an operator or administrator to individually select the responsiveness of the intent adaptations of the exoskeleton system 110.

Accordingly, in various embodiments, the exoskeleton system 110 can change the speed of adaptation of an intent recognition program running on the exoskeleton system 110, based at least in part on input received at an interface at the exoskeleton system 110, based at least in part on input received at an interface at a user device 120, and/or via instructions received from a classification server 130. In further embodiments, the exoskeleton system 110 can automatically tune the speed of adaptation of an intent recognition program running on the exoskeleton system 110, without user input, based on sensor data or the like. For example, a determination can be made that the intent recognition program is adapting too fast for a user based at least in part on sensor data and the exoskeleton system 110 can automatically slow the speed of the intent recognition program so that the exoskeleton system 110 adapts at a speed that better meets the needs of the user.

Figure 4:
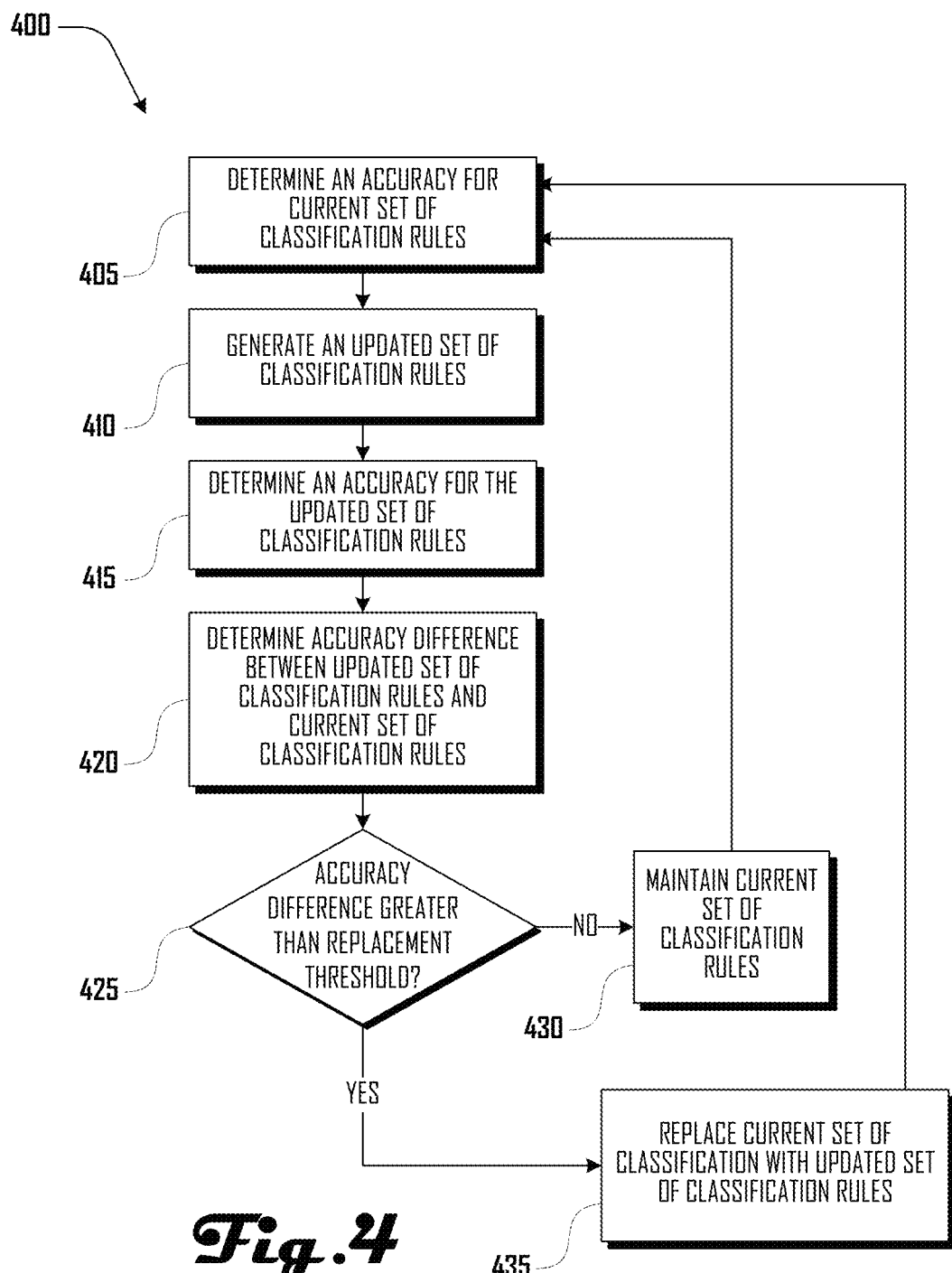
FIG. 4 illustrates an example method of updating a set of classification rules.

For example, FIG. 4 illustrates an example method 400 of updating a set of classification rules, which can be embodied in a classification program stored in the memory 312 of an exoskeleton system 110. The method 400 beings, at 405, where an accuracy is determined for a current set of classification rules. For example, a baseline accuracy can be determined by applying the current set of classification rules to determine an estimate of an exoskeleton system 110 device state or user state at the time of interest (t=0). In other examples, an accuracy can be determined based at least in part on historical data related to the current set of classification rules, which can include data regarding successful and unsuccessful classification attempts using the current set of classification rules. An accuracy can be based on a ratio of successful and unsuccessful classification attempts in various embodiments.

At 410, an updated set of classification rules can be generated. For example, an updated set of classification rules can be generated in various suitable ways including via random changes to the current classification rules, changes to the current classification rules based on one or more heuristics, and the like. In other words, an updated set of classification rules can comprise changes to or a delta of the current set of classification rules. In further embodiments, an updated set of classification rules can be generated, which is not based on a current set of classification rules. In other words, an updated set of classification rules or a portion thereof can be generated without reference to or without consideration of the current set of classification rules. In various embodiments, a reference set of classification rules or a reference classification program can be generated in a similar manner.

At 415, an accuracy for the updated set of classification rules can be determined. For example, where a baseline accuracy is determined by applying the current set of classification rules to determine an estimate of an exoskeleton system 110 device state or user state at the time of interest (t=0) as discussed above, and then the updated classification rules can be applied at a fixed time later (t=n) to determine an estimate of an exoskeleton system 110 device state or user state at the original time of interest (t=0) using additional sensor information collected the later time frame (t≥n) and/or before the later time frame (e.g., n≥t≥0).

In other examples, an accuracy of the updated set of classification rules can be determined based at least in part on historical data associated with the exoskeleton system 110, which can include making classification attempts using historical data, and then such attempts can be analyzed to determine whether such classification attempts where successful or unsuccessful. An accuracy of the updated classification rules can be based on a ratio of successful and unsuccessful classification attempts by the updated classification rules. For example, successful and unsuccessful classification attempts by the updated classification rules can be determined based on data such as data used to determine successful and unsuccessful classification attempts by the current classification rules.

In some examples, the updated classification rules can be temporary implemented one or more exoskeleton system 110 and the updated classification rules can be evaluated based on actual use of the one or more exoskeleton system 110. Additionally, while evaluation of current or updated rules can be based on data of a single exoskeleton system 110, in some examples, such evaluation can be based on historical data from a plurality of exoskeleton systems 110 (see e.g., FIG. 2).

Returning to FIG. 4, the method 400 continues to 420 where an accuracy difference between the updated set of classification rules and the current set of classification rules is determined, and at 425, a determination is made whether the accuracy difference is greater than a replacement threshold. If not, the current set of classification rules is maintained at 430, and if so, at 435, the current set of classification rules is replaced by the updated set of classification rules. For example, where the updated classification rules are determined to provide a substantial improvement over the current set of classification rules, the current classification rules can be replaced by the improved updated classification rules. As shown in FIG. 4, such a method 400 can iteratively improve a current set of classification rules. For example, after 430 and 435 the method 400 can cycle back to 405 where the new or maintained set of classification rules is again evaluated.

In further examples, where estimated exoskeleton system 110 device states and/or user states are determined for the current and updated sets of classification rules, such estimates can be compared. If the results from the current set of classification rules is different than the results from the updated set of classification rules (which can be more accurate in some examples) then the current set of classification rules can be adapted to develop a second updated set of classification rules that is designed to better determine the classification accuracy of the time of interest (t=0). The current set of classification rules can be updated with, or can be replaced by, the second updated set of classification rules.

Accordingly, in some embodiments, a method of updating a set of classification rules can comprising determining a first state estimate for a current classification program being implemented by the exoskeleton system 110; determining a second state estimate for a reference classification program; determining that the difference between the first and second state estimate is greater than a classification program replacement threshold; generating an updated classification program; and replacing the current classification program with the updated classification program, based at least in part on the determining that the difference between the first and second state estimates is greater than the classification program replacement threshold.

In various embodiments, such methods can be performed locally at an exoskeleton system 110, locally at a user device 120 and/or remotely at a classification server 130. Additionally, the method 300, or portions thereof, can be performed automatically without user input. For example, an exoskeleton system 110 can automatically improve classification rules that the exoskeleton system 110 uses during operation of the exoskeleton system 110 without input by the user, an administrator, or the like. Similarly, a user device 120 and/or classification server 130 can similarly automatically improve classification rules that the exoskeleton system 110 uses during operation of the exoskeleton system 110 without input by the user, an administrator, or the like. Such automation can be desirable for efficiently improving the functioning of one or more exoskeleton system 110 without the need for, or with the limited need for input from users or administrators. Additionally, while classification rules are discussed in various examples herein, it should be clear that such methods can be applied to a classification program, intent recognition program, or the like, that embodies, employs, or enforces such classification rules. In various embodiments, a classification program and intent recognition program can refer to the same type of program, method, algorithm, or the like.

Unsupervised refinement of the intent recognition programs can be executed for a variety of reasons. For example, one embodiment can refine the intent recognition classification behavior in order to improve the performance of the classification across a population of users. In this embodiment, the same classification program can be deployed to a plurality of exoskeleton systems 110 and use a large pool of available data collected across the set of exoskeleton systems 110 in use to increase performance of the exoskeleton systems 110.

Figure 5:
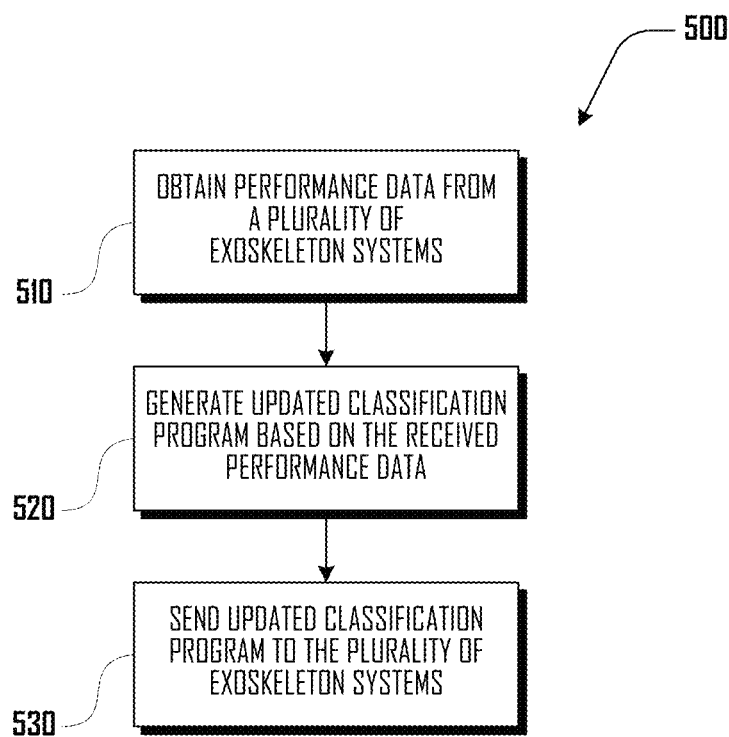
FIG. 5 illustrates an example method of improving classification programs of a plurality of exoskeleton systems.

For example, as illustrated in FIG. 5, an example method 500 of improving classification programs of a plurality of exoskeleton systems 110 can begin at 510 where performance data is obtained from a plurality of exoskeleton systems 110. At 520, an updated classification method is generated based on the received performance data, and at 530, the updated classification program is sent to the plurality of exoskeleton systems 110. For example, in some embodiments, the method 500 can be performed by a classification server 130 (see, e.g., FIG. 2). However, in some embodiments, the method 500 can be implemented by a user device 120 and/or at one or more exoskeleton systems 110. Additionally, generating an updated classification program can include various suitable steps, including steps as described above in the method 400 of FIG. 4.

In another embodiment, the behavior of intent recognition programs can be refined to allow the performance of a specific exoskeleton system 110 to perform better for an individual user. Such an embodiment can refine the behavior of the intent recognition to improve the accuracy or the responsiveness of the classifications over time for the specific exoskeleton system 110. The specifics of these improved recognition behaviors for the specific exoskeleton system 110 can then be stored (e.g., on one or more local device such as in the memory 312 of the exoskeleton system 110, at a user device 120 and/or one or more remote device such as a classification server 130 or user device 120) for deployment onto a replacement exoskeleton system 110 or a different specific exoskeleton system 110 altogether to allow these specific exoskeleton system 110 to know the movements and preferences of the specific user.

Yet another embodiment can refine the behavior of an intent recognition program to accommodate changes in the response of sensors 313 of an exoskeleton system 110 over time. These updates to an intent recognition program can be designed to account for the normal variation of sensor behavior over time, to address the catastrophic failure of a sensor 313, and the like.

Figure 6:
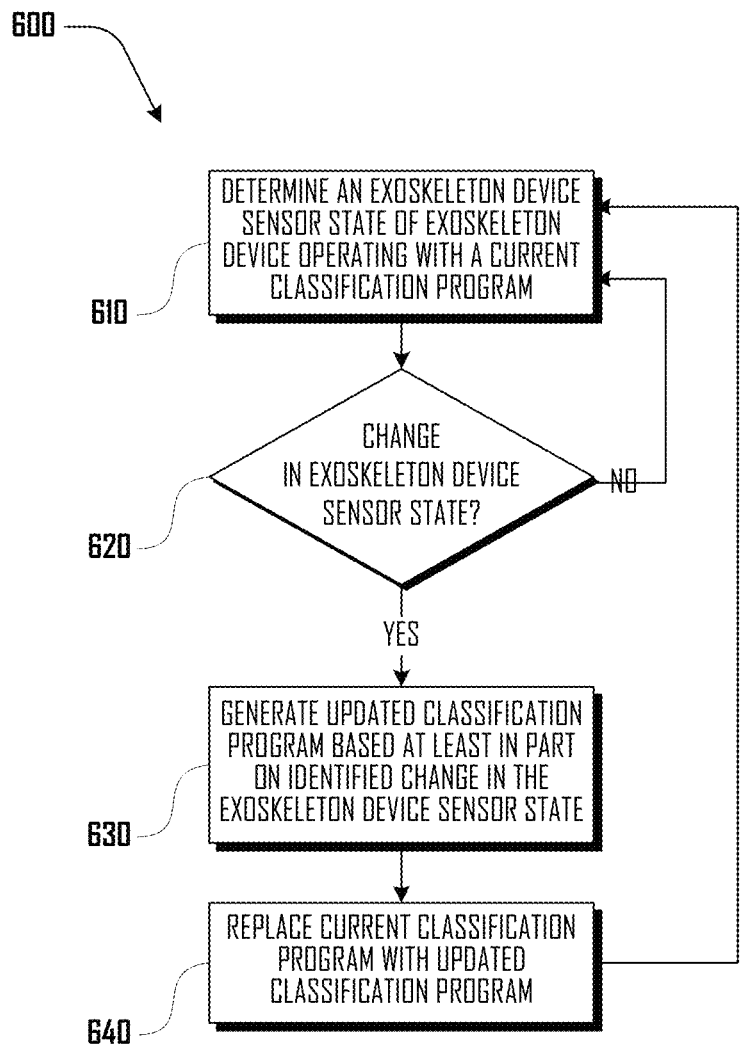
FIG. 6 illustrates an example method of updating a classification program based on the state of one or more sensors of an exoskeleton system.

For example, FIG. 6 illustrates an example method 600 of updating a classification program based on the state of one or more sensors 313 of an exoskeleton system 110. The method 600 begins at 610 where an exoskeleton device sensor state is determined for an exoskeleton system 110 operating with a current classification program. At 620, a determination is made whether there is a change in the exoskeleton state. For example, a change in the state of one or more sensors 313 can include the sensor being operative/inoperative, change in calibration state, change in sensor accuracy, change in sensor physical position on the exoskeleton system 110, and the like. In some embodiments, a sensor state change can be associated with changes in parts of an exoskeleton system 110, including a change in one or more actuator 305, pneumatic system 320, pneumatic line 330, and the like. For example, problems, deterioration and/or material changes of parts of an exoskeleton system 110 can be associated with a change in a sensor state.

Where a change in the exoskeleton device sensor state is not identified in 620, the method 600 cycles back to 610, where exoskeleton device sensor state continues to be monitored. However, where a change in the exoskeleton device sensor state is identified in 620, the method 600 continues to 630, where an updated classification program is generated based at least in part on the identified change in the exoskeleton device sensor state, and at 640, the current classification program is replaced by the updated classification program.

For example, where changes in an exoskeleton system 110 result in sensors reporting sensor data differently, the current classification program of the exoskeleton system 110 may lose accuracy because it is not tuned to the changes in sensor data being ingested by the current classification program. Accordingly, such a change in exoskeleton device sensor state can be identified and a current classification program can be replaced with an updated classification program that is tuned to the change in the exoskeleton device sensor state.

For the performance of these programs, the specifics of the intent recognition classifier designs can have a significant impact on the performance of the programs in some embodiments. It is important to note that the specific classification program does not limit the application of the described methods in accordance with various embodiments. The use of the term classification or classifier within this description is used to denote an algorithm, program or method that specifies the intent of an operator of an exoskeleton system 110 at a certain time being considered. The classification program can include, but is not limited to, support vector machines, neural networks, linear discriminant analysis, quadratic discriminant analysis, dynamic bayes nets, hidden markov models, or the like.

For clarity, the programs used to recognize exoskeleton system user intent can be configured to identify a wide array of motions from the operator of an exoskeleton system 110. These can include motions, maneuvers, movements, stances, gaits, or the like, that are consciously and/or subconsciously executed by the operator. The specific motions that these intent recognition programs can be consider, analyze, classify, or the like, can include but are not limited to walking, standing, running, jumping, squatting, ascending stairs, descending stairs, landing, turning, sitting, grasping, reaching, or the like. Similarly, these intent recognition programs can be applied to identify mid-maneuver phases of the gait that may be important, which can include but are not limited to heel strike, mid stance, late stance, toe off, flight, ascending, descending, or the like.

The introduction of such new adaptive intent recognition programs can require new methods for the user to interact with the exoskeleton system 110 in some embodiments. For example, an embodiment can provide the user with manual intent override behaviors that the user can use to force the intent recognition program into a desired behavior in the event that it is not behaving as expected or desired. Another set of embodiments can include user feedback that allows the operator of an exoskeleton system 110 to influence the learning behavior of the data driven programs.

One such embodiment of feedback can provide the operator with manual choices to aid in refining performance of the exoskeleton system 110 through defining new behaviors that the exoskeleton system 110 has seen. For example, if an instantaneous classifier program believes the person is moving from standing to ascending stairs, but a foresight classifier program believes the person actually transitioned to squatting, the exoskeleton system 110 may find it useful to allow the user to confirm this change in performance.

Figure 7:
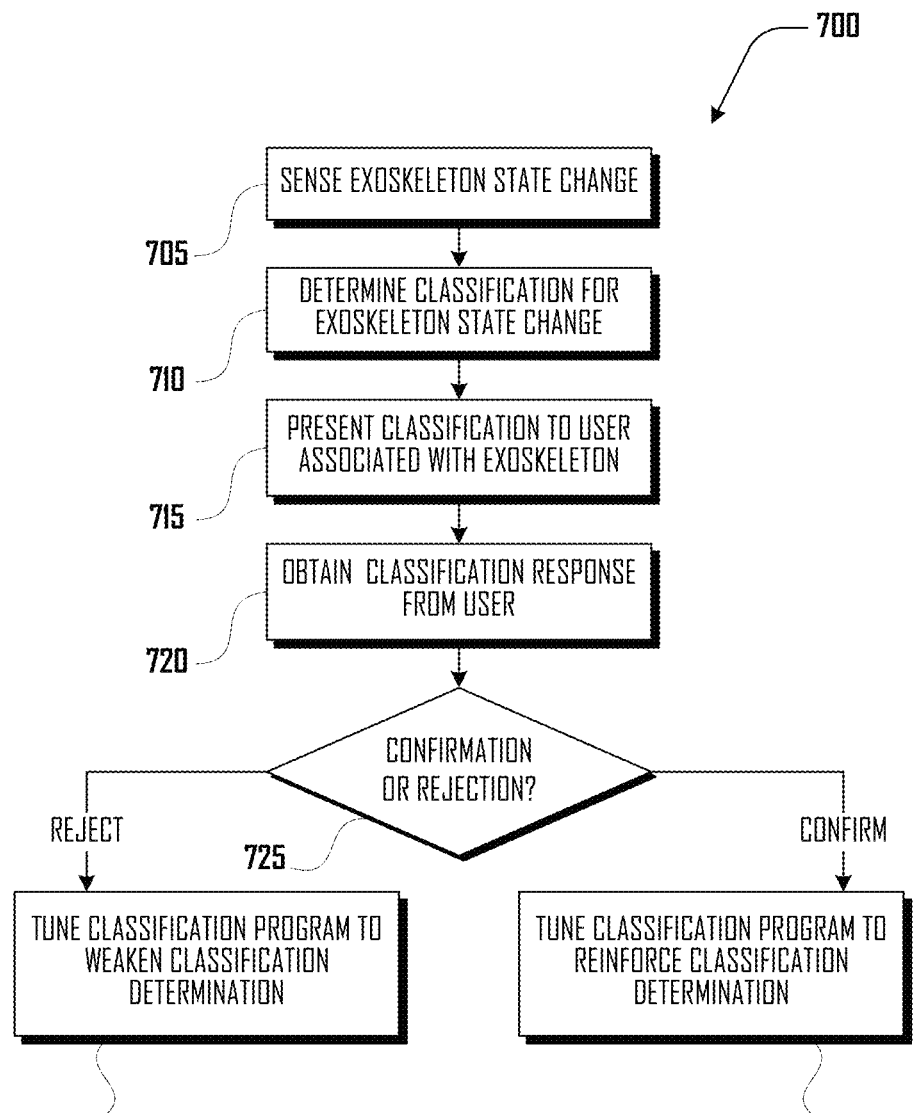
FIG. 7 illustrates an example method of tuning a classification program based at least in part on a user response to a classification determination.

For example, FIG. 7 illustrates an example method 700 of tuning a classification program based at least in part on a user response to a classification determination. The method 700 beings at 705, where a state change in an exoskeleton system 110 is sensed, and at 710, a classification for the sensed state change is determined. For example, the exoskeleton system 110 can obtain data from sensors 313 that is indicative of a user of the exoskeleton system 110 initiating new movement or a changing of movements. The classification program of the exoskeleton system 110 can classify the new movement.

At 715 the classification is presented to a user associated with the exoskeleton system 110, and at 720, a classification response is obtained from the user associate with the exoskeleton system 110. For example, in some embodiments a classification can be presented on a display (e.g., of a user device 120, exoskeleton device 310, or the like), and a user can provide a response (e.g., indicating rejection or confirmation of the classification) via a user input such as a touch screen, button, or the like. A user being presented the classification and/or providing a response to the classification can be a user wearing the exoskeleton system 110, an administrator working with user wearing the exoskeleton system 110, or the like.

At 725, a determination is made whether the classification response is a confirmation or a rejection, and if the user response is a rejection of the classification determination, then at 730 the classification program is tuned to weaken the classification determination. However, if the user response is a confirmation of the classification determination, then at 730 the classification program is tuned to strengthen the classification determination. For example, where the user confirms a classification determination, the classification program can be changed to reinforce the determination method used to make the classification determination. In another example, the where the user confirms a classification determination a record can be made of a successful classification, and if not, then a record of an unsuccessful classification can be generated. Such records of successful and unsuccessful classifications can be used as discussed herein (e.g., in method 300 discussed above).

While many items may be influential in determining the reason for seeking user confirmation, one metric can be to ask for confirmation whenever the refined classification is moving to a device state where the device will perform substantially different than it had under the original behavior. In other words, in some embodiments, user confirmation can be limited to changes in exoskeleton state that are above a threshold defines substantial changes compared to insubstantial changes.

Figure 8:
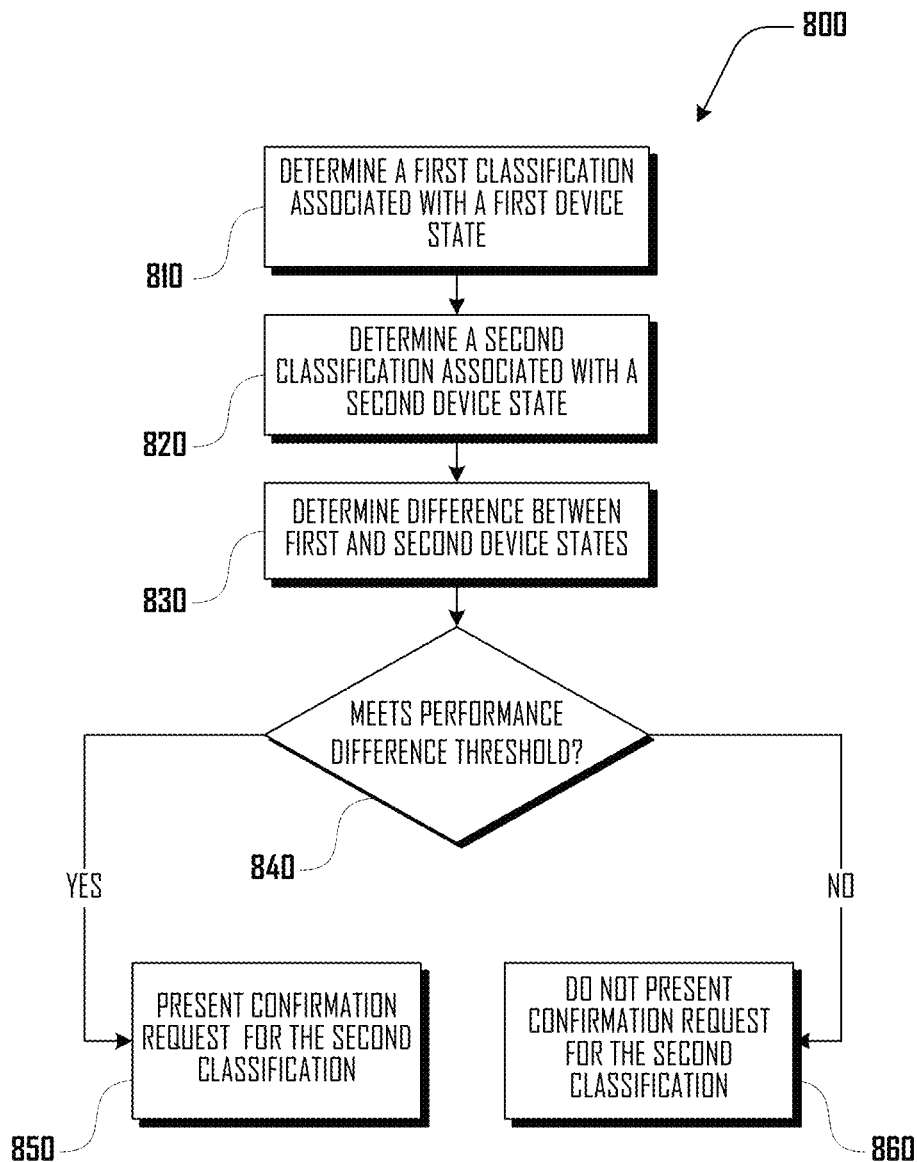
FIG. 8 illustrates a method of determining whether to present a confirmation request for a classification determination.

For example, FIG. 8 illustrates a method 800 of determining whether to present a confirmation request for a classification determination. The method 800 begins at 810 where a first classification associated with a first device state is determined, and at 820, a second classification associated with a second device state is determined. At 830, a difference between the first and second device state is determined, and at 840, a determination is made whether the difference between the first and second device state is above a performance difference threshold. For example, in some embodiments, the difference can be above a performance difference threshold where a second behavior classification is moving to an exoskeleton state where the exoskeleton device will perform substantially different than it had under a first behavior classification.

If the difference between the first and second device state is determined to be above the performance difference threshold, then at 830, a confirmation request for the second classification is presented to a user. For example, see step 710 of the method 700 of FIG. 7. However, if the difference between the first and second device state is determined to not be above the performance difference threshold, then at 835, a confirmation request for the second classification is not presented to the user.

Another embodiment can provide the user with feedback that is tailored towards experience of the device such as manipulating the balance between classification accuracy and classification delay. For example, if the user is interested in maximizing performance but is in a safe scenario where they can absorb a higher potential of classification error, the user may elect to have the exoskeleton system 110 make intent recognition decisions with a lower level of confidence to get the exoskeleton system 110 to respond as fast as possible. For the purpose of clarity, the medium for these feedback features is not of specific importance in various embodiments. The feedback can be initiated by the user through a variety of input methods which include but are not limited to a cell phone, a personal computer, a remote control, a wearable companion controller, or the like (e.g., via the exoskeleton system 110 and/or user device 120). Additionally, input from a user can be provided in various suitable ways, including via a physical input such as a touch screen, buttons, an audio input (e.g., voice commands), or the like. Similarly, presentations to a user can be provided in various suitable ways with various suitable interfaces, including via a screen, audio output, haptic feedback, or the like.

Similar to how these new programs can require new interactions for users in the exoskeleton system 110, in some embodiments, such new programs can also introduce the need for new interactions for developers or end users that allow them to understand how the exoskeleton system 110 is operating. One embodiment includes a user interface that demonstrates to the interested party the performance of the exoskeleton system 110. For example, the user interface can graphically depict the allowable maneuver transitions and identify the transitions that the exoskeleton system 110 has demonstrated a low chance of accurately classifying. Other embodiments can include information regarding the accuracy of these intent recognition classifications over time. Still other embodiments can provide insight on how to improve the performance of the intent recognition program performance, through identifying a specific maneuver where not enough information has been collected yet or by identifying changes in exoskeleton system 110 behaviors that may be leading to changes in intent recognition program performance.

Other embodiments can provide feedback to the designers of exoskeleton systems 110 as to which sensors 313 have the greatest impact on the performance of the exoskeleton system 110. For example, if the designer has visualized the transition of the exoskeleton system 110 and is attempting to improve the accuracy of a specific transition. The user interface can suggest the addition of other sensors 313, or sensor accuracies, that have shown to improve this classification in previous training examples.

For the purpose of clarity, various examples of this disclosure are focused toward the design and implementation of exoskeleton systems 110; however, further examples have application to a wide range of worn devices where the device is using onboard sensors for the purpose of recognizing the intended behavior of a user. A specific example of this is footwear, specifically the potential of active footwear, where the device uses included sensors to determine the intended behavior of the operator such that it can report statistics, or adapt the performance characteristics for the user.

The methods described herein can be employed in various suitable operating environments. For example, embodiments can comprise an exoskeleton system 110 that includes one or more sensors 313 disposed about the exoskeleton device and configured to sense various states of the exoskeleton system 110, including movement, rotation, acceleration, orientation, temperature, or the like. As discussed herein, such an exoskeleton system 110 can be associated with one or more body parts of a user. For example, some embodiments can be associated only with the legs of a user, whereas others can be associated with the legs, torso and arms.

The exoskeleton system 110 can comprise one or more actuators configured to move the exoskeleton system 110 in various suitable ways. Such actuators can include fluidic actuators (e.g., actuators 305), motor actuators, or the like. The exoskeleton system 110 can also comprise a control system operable to control the actuators and such a control system can be operably coupled to the sensors and actuators. The exoskeleton system 110 can also comprise components such as a power source, processor 311 and memory 312 with software or firmware that is operable to perform at least a part of the methods described herein.

Figure 9:
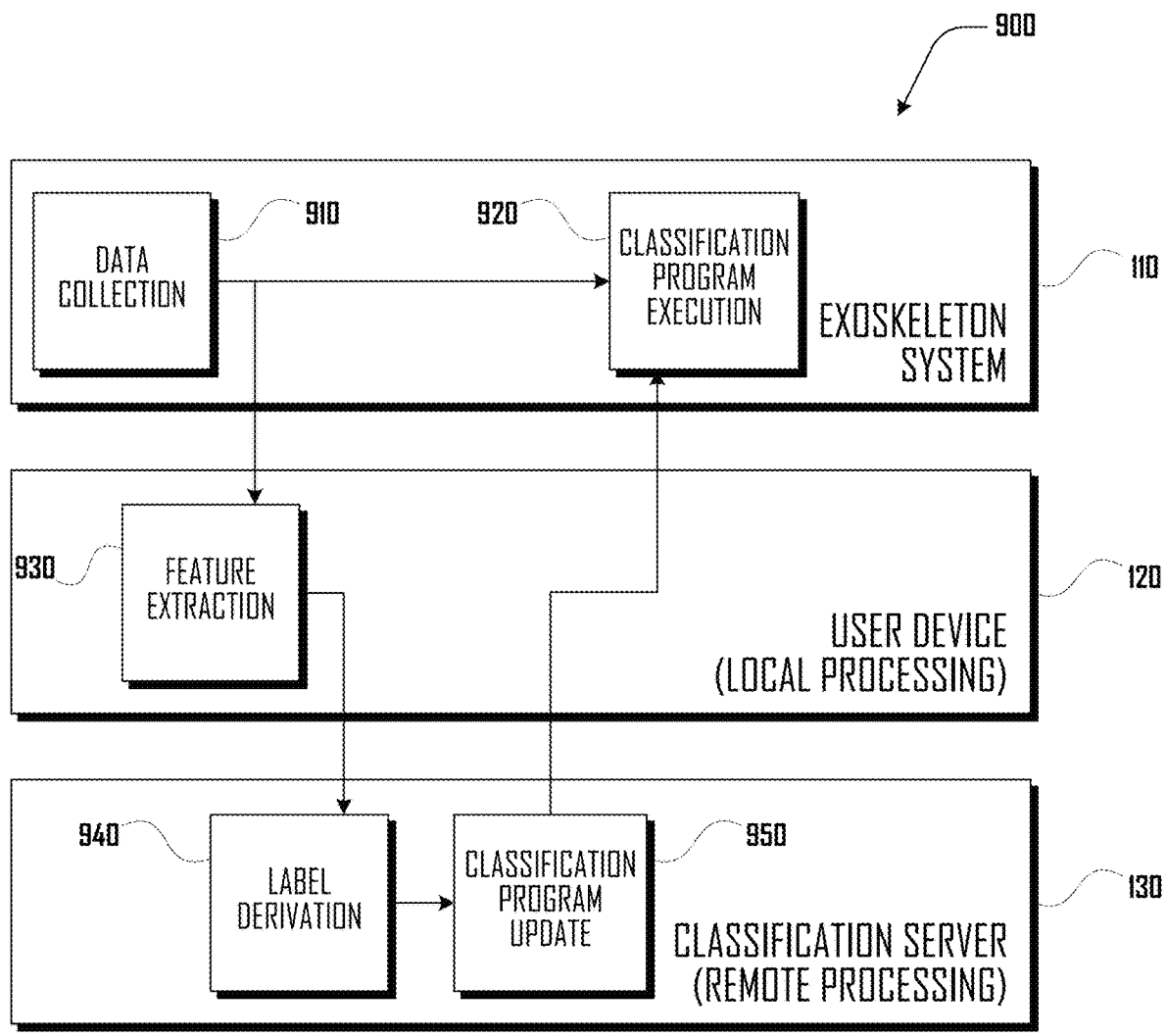
FIG. 9 illustrates one embodiment of an exoskeleton processing network comprising three processing levels.

Some embodiments can include a plurality of processing levels. For example, FIG. 9 illustrates one embodiment of an exoskeleton processing network 900 comprising three processing levels. A first architectural level of the network 900 can comprise local processing elements on an exoskeleton system 110, including a data collection process 910 and a classification program execution process 920. For example, the data collection process 910 can obtain and process data obtained from sensors 313 (see, e.g., FIG. 3), and send such processed data to the classification execution process 920, which runs a classification program, which can include a classification program as discussed herein. Various embodiments can implement the processing at the exoskeleton system 110 through a variety of methods, including but not limited to, a single centralized embedded DSP, a set of distributed processors, background calculation processes, in real time processes, or the like.

A second architectural level of the network 900 can comprise a nearby secondary processing unit, which can include a user device 120 or the like (See, e.g., FIG. 1). The user device can execute a feature extraction process 930, which receives data from the data collection process 910 at the exoskeleton system 110, performs actions including feature extraction, and the like. As discussed herein, this user device 120 can be operably coupled to the exoskeleton system 110 through a suitable communication channel such as a Bluetooth connection, or the like. This second layer can be operated on a processing unit that can be overseen by the user of the user device 120. This second layer can be operated on various suitable user devices 120 as discussed herein, including a cell phone, a personal computer, or the like.

A third processing level can comprise a network-based processing system such as a classification server 130 (see e.g. FIGS. 1 and 2) that is remote to the user device 120 and exoskeleton system 110, and in various embodiments, not directly controlled by the user of the exoskeleton system 110 and user device 120. The third processing level at the classification server 130 can include a label derivation process 940 that receives data from the feature extraction process 930 at the user device 120, and performs label derivation on the received data. Date resulting from label derivation at the label derivation process 940 can be provided to a classification program update process 950 that generates an updated classification program based at least in part on data generated by label derivation process 940. The classification program update process 950 can send updated classification program data to the user device 120, and the user device 120 can send the updated classification program data to the classification program execution process 920 at the exoskeleton system 110, where a current classification program being executed by the classification program execution process 920 can be replaced with an updated classification program embodied in the received updated classification program data.

For clarity, other embodiments can add to, remove, or reconfigure the aspects of the example processing layers shown in FIG. 9. Accordingly, the present example should not be construed to be limiting on the wide variety of alternative embodiments that are within the scope and spirit of the present disclosure.

Various embodiments can comprise a number of discrete processes. These can include a data collection process 910, a feature extraction process 930, a label derivation process 940, a classification program update process 950, a classification program execution process 920, and the like. While some of these example discrete processes can be executed on specific processing units as shown in the example of FIG. 9, some processes can be architected and processed in a variety of processing levels. For example, the data collection process 910 and classification program execution process 920 can be executed on the user device 120, with other processes deployed on other processing levels, including at the classification server 130 or exoskeleton system 110. Accordingly, while a specific example is illustrated in FIG. 9, other suitable configurations of processes are within the scope and spirit of the present disclosure.

Another aspect of this disclosure is with regards to the frequency and distribution of the classification program updates. In many embodiments, the value of the classification program update can be provided through regular distribution of improved classification programs. In many cases, this can be driven due to the high capital costs associated with the hardware of most conventional exoskeletons 110. However, in some embodiments, the cost of hardware can change the highest value distribution method. In this embodiment, it may prove to be most valuable for the and update method to harvest data off devices that are in the field and then update the classification program, but only deploy the updated classification programs on new versions of the hardware.

One embodiment can use footwear as the device hardware. In this embodiment, the hardware distributor may use the updated algorithms to drive adoption of their new version of footwear as their business model centers around annual model sales. This embodiment can still make full use of features of embodiments described herein and in related patent application 62/454,575 referenced above, however, it can use a discrete deployment architecture that is deploying intent classification program that have been trained through unsupervised learning onto new hardware as opposed to the old hardware that is expected to go obsolete within a few months.

Turning to FIG. 10, one embodiment 110E of a pneumatic exomuscle system 110 is shown as comprising a plurality of actuators 305 disposed at locations of a shirt 1020 that is being word by a user 1001. A shoulder-actuator 305S is shown positioned over the shoulder 1005 of the user 1001. An elbow-actuator 305E is shown positioned over the elbow 1003 of the user 1001. A wrist-actuator 305W is shown positioned over the wrist 1004 of the user 1001.

Similarly, FIG. 11 illustrates another embodiment 110F of a pneumatic exomuscle system 110 that is shown comprising a plurality of actuators 305 disposed at locations on leggings 1120 that are being worn on the legs 1101 of a user 1001. An anterior knee-actuator 305KA and posterior knee-actuator 305KP are shown positioned on respective anterior 1102A and posterior 1102P sides of the knee 1102 of the user 1001. An anterior hip-actuator 305HA and posterior hip-actuator 305HP are shown positioned on respective anterior 1103A and posterior 1103P sides of the hip 1103 of the user 1001. An ankle actuator 305A is shown positioned on the ankle 1104 of the user 1001

Although FIGS. 10 and 11 illustrate separate top and bottom suits 110E, 110F, in various embodiments the pneumatic exomuscle system 110 can be configured to cover the entire body of a user 1001 or portions of the body a user 1001. For example, the pneumatic exomuscle system 110 can be embodied in a complete body suit, an arm sleeve, a leg sleeve, a glove, a sock, or the like. Additionally, although actuators 305 are depicted being positioned over the elbow 103, wrist 104, shoulder 105, knee 1102, hip 1103 and ankle 1104, any one or more of these actuators 305 can be absent and/or additional actuators 305 can be present in any other suitable location. For example, actuators 305 can be present on hands, feet, neck, torso, or the like. FIG. 12 illustrates one example embodiment 110G of an exoskeleton system 110 that includes ankle actuators 305A positioned on the ankles 1104 of the user 1001

Furthermore, the present disclosure discusses various embodiments of the pneumatic exomuscle system 110 being worn by a human user 1001, but in further embodiments, the pneumatic exomuscle system 110 can be adapted for use by non-human users (e.g., animals) or adapted for non-living devices such as robots or the like. For example, one embodiment includes the use of the pneumatic exomuscle system 110 and/or one or more actuator 305 in a robotic arm not worn on the body 1001, which is also known as a robotic manipulator.

The described embodiments are susceptible to various modifications and alternative forms, and specific examples thereof have been shown by way of example in the drawings and are herein described in detail. It should be understood, however, that the described embodiments are not to be limited to the particular forms or methods disclosed, but to the contrary, the present disclosure is to cover all modifications, equivalents, and alternatives.

What is claimed is:

1. An exoskeleton network comprising:
    a wearable pneumatic exoskeleton system that includes:
        a plurality of pneumatic actuators configured to be associated with body parts of a user wearing the wearable pneumatic exoskeleton system,
        a pneumatic system configured to introduce pneumatic fluid to the plurality of pneumatic actuators to actuate the plurality of pneumatic actuators, and
        an exoskeleton computing device including:
            a plurality of sensors,
            a memory storing at least a classification program, and
            a processor that executes the classification program that controls the pneumatic system based at least in part on classifications generated by the classification program, of sensor data obtained from the plurality of sensors;
    a user device that is local to the wearable pneumatic exoskeleton system and that operably communicates with the wearable pneumatic exoskeleton system; and
    a classification server that is remote from the user device and wearable pneumatic exoskeleton system and that operably communicates with the wearable pneumatic exoskeleton system and the user device,
    wherein the exoskeleton network:
        processes, at the wearable pneumatic exoskeleton system, at least a portion of the sensor data obtained from the plurality of sensors to generate processed sensor data;
        sends, by the wearable pneumatic exoskeleton system, the processed sensor data to the user device;
        performs, by the user device, feature extraction on the processed sensor data to generate feature-extracted sensor data;
        sends, by the user device, the feature-extracted sensor data to the classification server;
        performs, by the classification server, label derivation on the feature-extracted sensor data to generate labeled sensor data;
        generates, by the classification server, updated classification program data based at least in part on the labeled sensor data;
        sends, by the classification server, the updated classification program data to the user device;
        sends, by the user device, the updated classification program data received from the classification server, to the wearable pneumatic exoskeleton system; and
        replaces, by the wearable pneumatic exoskeleton system, in the memory of the wearable pneumatic exoskeleton system, a current classification program with an updated classification program embodied in the updated classification program data received from the user device.

2. The exoskeleton network of claim 1, further comprising a plurality of wearable pneumatic exoskeleton systems that operably communicate with the classification server, each of the plurality of wearable pneumatic exoskeleton systems including:
    a plurality of pneumatic actuators configured to be associated with body parts of a user wearing the wearable pneumatic exoskeleton system,
    a pneumatic system configured to introduce pneumatic fluid to the plurality of pneumatic actuators to actuate the plurality of pneumatic actuators, and
    an exoskeleton computing device including:
        a plurality of sensors,
        a memory storing at least a classification program, and
        a processor that executes the classification program that controls the pneumatic system based at least in part on classifications by the classification program, of sensor data obtained from the plurality of sensors,
    wherein each of the plurality of wearable pneumatic exoskeleton systems is configured to:
        process, at the wearable pneumatic exoskeleton system, at least a portion of the sensor data obtained from the plurality of sensors to generate processed sensor data;
        send, by the wearable pneumatic exoskeleton system, the processed sensor data to user device that is local to the wearable pneumatic exoskeleton system and that operably communicates with the wearable pneumatic exoskeleton system,
        receive at the wearable pneumatic exoskeleton system, from the user device, the updated classification program data generated at the classification server, to the wearable pneumatic exoskeleton system; and
        replace, by the wearable pneumatic exoskeleton system, in the memory of the wearable pneumatic exoskeleton system, a local current classification program with an updated classification program embodied in the updated classification program data received from the user device.

3. The exoskeleton network of claim 1, wherein the classification server comprises one or more virtual or non-virtual servers that are remote from the user device and wearable pneumatic exoskeleton system and that operably communicate with at least one of the wearable pneumatic exoskeleton system and the user device via the Internet, and wherein the classification server is not directly controllable by a user that is able to control the wearable pneumatic exoskeleton system and user device.

4. The exoskeleton network of claim 1, wherein the wearable pneumatic exoskeleton system is configured to communicate with the user device only via a direct local connection and inoperable to communicate via a long-distance network that allows the user device and classification server to communicate.

5. The exoskeleton network of claim 1, wherein the user device is a smartphone or is an integral part of the wearable pneumatic exoskeleton system.

6. An exoskeleton network comprising:
an exoskeleton system that includes:
a plurality of actuators configured to be associated with body parts of a user wearing the exoskeleton system, and
an exoskeleton computing device including:
a plurality of sensors,
a memory storing at least a classification program, and
a processor that executes the classification program that controls the plurality of actuators based at least in part on classifications generated by the classification program, of sensor data obtained from the plurality of sensors;
a user device that is local to the exoskeleton system and that operably communicates with the exoskeleton system; and
a classification server that is remote from the user device and exoskeleton system and that operably communicates with at least one of the exoskeleton system and the user device,
wherein the exoskeleton network:
processes at least a portion of the sensor data obtained from the plurality of sensors to generate processed sensor data;
performs feature extraction on the processed sensor data to generate feature-extracted sensor data;
performs, by the classification server, label derivation on the feature-extracted sensor data to generate labeled sensor data for use in reconsidering classification of one or more maneuvers by the user wearing the exoskeleton system after the one or more maneuvers have already been classified by the exoskeleton system;
generates, by the classification server, an updated classification program based at least in part on:
the labeled sensor data, and
reconsideration of classification of one or more maneuvers by the user wearing the exoskeleton system after the one or more maneuvers have already been classified by the exoskeleton system;
sends, by the classification server, the updated classification program data to the user device or to the exoskeleton computing device; and
replaces in the memory of the exoskeleton system, a current classification program being used by the exoskeleton system, with the updated classification program generated by and obtained from the classification server.

7. The exoskeleton network of claim 6, wherein the user device performs the feature extraction on the processed sensor data to generate the feature-extracted sensor data.

8. The exoskeleton network of claim 6, wherein the classification server performs the label derivation on the feature-extracted sensor data to generate the labeled sensor; and
wherein the classification server generates the updated classification program based at least in part on the labeled sensor data.

9. The exoskeleton network of claim 8, wherein the classification server sends the updated classification program to the exoskeleton system via the user device.

10. The exoskeleton network of claim 6, wherein the classification server is not directly controllable by the user that is able to control the exoskeleton system and the user device.

11. The exoskeleton network of claim 6, wherein the classification server comprises one or more virtual or non-virtual servers that are remote from the user device and exoskeleton system and that operably communicate with at least one of the exoskeleton system and the user device via the Internet.

12. The exoskeleton network of claim 6, wherein the exoskeleton system is configured to communicate with the user device only via a direct local connection and not via a long-distance network that allows the user device and classification server to communicate and wherein the exoskeleton system is inoperable to communicate with the user device via the long-distance network that allows the user device and classification server to communicate.

13. The exoskeleton network of claim 6, wherein the user device is a smartphone or is an integral part of the exoskeleton system.

14. An exoskeleton network comprising:
an exoskeleton system that includes:
one or more sensors, and
a memory;
a user device that is local to the exoskeleton system and that operably communicates with the exoskeleton system; and
a classification server that operably communicates with at least one of the exoskeleton system and the user device,
wherein the exoskeleton network:
performs feature extraction on sensor data obtained from the one or more sensors to generate feature-extracted sensor data;
performs, by the classification server, label derivation on the feature-extracted sensor data to generate labeled sensor data; and
replaces in the memory of the exoskeleton system, a current classification program with an updated classification program that was generated by the classification server based at least in part on:
the labeled sensor data, and
reconsideration of classification of one or more maneuvers by the user wearing the exoskeleton system after the one or more maneuvers have already been classified by the exoskeleton system.

15. The exoskeleton network of claim 14, wherein the exoskeleton network:
generates the current classification program and/or the updated classification program based at least in part on the labeled sensor data; and
stores the current classification program and/or the updated classification program in the memory of the exoskeleton system.

16. The exoskeleton network of claim 15, wherein the classification server generates the current classification program and/or the updated classification program based at least in part on the labeled sensor data, and
  wherein the classification server sends the current classification program and/or the updated classification program to the exoskeleton system to store the current classification and/or the updated classification program in the memory of the exoskeleton system.

17. The exoskeleton network of claim 14, wherein the user device performs the feature extraction on the sensor data to generate the feature-extracted sensor data.

18. The exoskeleton network of claim 14, wherein the classification server is not directly controllable by a user that is able to control the exoskeleton system and the user device.

19. The exoskeleton network of claim 14, wherein the classification server comprises one or more virtual or non-virtual servers that are remote from the user device and exoskeleton system and that operably communicate with at least one of the exoskeleton system and the user device via a long-distance network; and
  wherein the exoskeleton system is configured to communicate with the user device only via a direct local connection and not via the long-distance network that allows the user device and classification server to communicate.

20. The exoskeleton network of claim 14, wherein the user device is a smartphone or is a part of the exoskeleton system.

* * * * *

UNITED STATES PATENT AND TRADEMARK OFFICE
CERTIFICATE OF CORRECTION

PATENT NO. : 12,377,010 B2  
APPLICATION NO. : 16/862400  
DATED : August 5, 2025  
INVENTOR(S) : Timothy Alan Swift et al.

Page 1 of 1

It is certified that error appears in the above-identified patent and that said Letters Patent is hereby corrected as shown below:

On the Title Page

On Page 2, Item (60) should read:
-- Provisional application No. 62/485,284, filed on Apr. 13, 2017, provisional application No. 62/454,575, filed on Feb. 3, 2017. --

Signed and Sealed this
Sixteenth Day of September, 2025

Coke Morgan Stewart
*Acting Director of the United States Patent and Trademark Office*